US012611496B2

(12) United States Patent
Manda et al.

(10) Patent No.: US 12,611,496 B2
(45) Date of Patent: Apr. 28, 2026

(54) PERITONEAL DIALYSATE FLUID GENERATION SYSTEM

(71) Applicant: MOZARC MEDICAL US LLC, Minneapolis, MN (US)

(72) Inventors: VenKatesh R. Manda, Stillwater, MN (US); Martin T. Gerber, Maple Grove, MN (US); Christopher M. Hobot, Rogers, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 0 days.

(21) Appl. No.: 16/455,822

(22) Filed: Jun. 28, 2019

(65) Prior Publication Data

US 2019/0321536 A1      Oct. 24, 2019

Related U.S. Application Data

(63) Continuation of application No. 15/478,562, filed on Apr. 4, 2017.
(Continued)

(51) Int. Cl.
*A61M 1/28*          (2006.01)
*A61K 31/19*          (2006.01)
(Continued)

(52) U.S. Cl.
CPC ............ *A61M 1/282* (2014.02); *A61K 31/19* (2013.01); *A61K 31/7004* (2013.01); *A61K 31/716* (2013.01); *A61K 33/00* (2013.01); *A61K 33/06* (2013.01); *A61K 33/14* (2013.01); *A61L 2/0017* (2013.01); *A61L 2/0023* (2013.01); *A61L 2/0047* (2013.01); *A61M*

*1/1656* (2013.01); *A61M 1/1672* (2014.02); *A61M 1/1674* (2014.02); *A61M 1/1686* (2013.01); *A61M 1/28* (2013.01); *A61M 1/287* (2013.01); *C02F 1/001* (2013.01); *C02F 1/02* (2013.01); *C02F 1/28* (2013.01);
(Continued)

(58) Field of Classification Search
None
See application file for complete search history.

(56) References Cited

U.S. PATENT DOCUMENTS 2,002 A      3/1841    Rider
3,602,222 A      8/1971    Herndon
(Continued)

FOREIGN PATENT DOCUMENTS

CN          1273535          11/2000
CN          1643368 A        7/2005
(Continued)

OTHER PUBLICATIONS

European Office Action for App. No. 17718246.6, dated Apr. 2, 2020.
(Continued)

*Primary Examiner* — Jonathan M Peo

(57) ABSTRACT

Systems and methods of generating peritoneal dialysate are provided. The systems and methods use a water purification module, a sterilization module and concentrates to prepare a bolus of peritoneal dialysate from source water for use with a non-integrated cycler. The systems and methods use at least two concentrate sources to generate a peritoneal dialysate.

20 Claims, 15 Drawing Sheets

Related U.S. Application Data

(60) Provisional application No. 62/318,169, filed on Apr. 4, 2016.

(51) Int. Cl.

| | |
|---|---|
| *A61K 31/7004* | (2006.01) |
| *A61K 31/716* | (2006.01) |
| *A61K 33/00* | (2006.01) |
| *A61K 33/06* | (2006.01) |
| *A61K 33/14* | (2006.01) |
| *A61L 2/00* | (2006.01) |
| *A61M 1/14* | (2006.01) |
| *A61M 1/16* | (2006.01) |
| *C02F 1/00* | (2023.01) |
| *C02F 1/02* | (2023.01) |
| *C02F 1/28* | (2023.01) |
| *C02F 1/32* | (2023.01) |
| *C02F 1/42* | (2023.01) |
| *C02F 1/44* | (2023.01) |

(52) U.S. Cl.

CPC ............. *C02F 1/283* (2013.01); *C02F 1/325* (2013.01); *C02F 1/42* (2013.01); *C02F 1/441* (2013.01); *C02F 1/442* (2013.01); *C02F 1/444* (2013.01); *A61L 2202/21* (2013.01); *A61M 1/159* (2022.05); *A61M 1/1666* (2014.02); *A61M 2205/3337* (2013.01); *A61M 2205/3584* (2013.01); *A61M 2205/50* (2013.01); *A61M 2205/502* (2013.01); *A61M 2205/75* (2013.01); *A61M 2205/7518* (2013.01); *A61M 2209/10* (2013.01); *C02F 2303/04* (2013.01)

(56) References Cited

U.S. PATENT DOCUMENTS

| | | | |
|---|---|---|---|
| 3,608,729 A | 9/1971 | Haselden | |
| 3,669,878 A | 6/1972 | Marantz | |
| 3,669,880 A | 6/1972 | Marantz | |
| 3,730,183 A | 5/1973 | Goldsmith | |
| 3,754,867 A * | 8/1973 | Guenther | G01N 21/783 |
| | | | 436/163 |
| 3,850,835 A | 11/1974 | Marantz | |
| 3,884,808 A | 5/1975 | Scott | |
| 3,989,622 A | 11/1976 | Marantz | |
| 3,989,625 A | 11/1976 | Mason | |
| 4,060,485 A | 11/1977 | Eaton | |
| 4,371,385 A | 2/1983 | Johnson | |
| 4,374,382 A | 2/1983 | Markowitz | |
| 4,381,999 A | 5/1983 | Boucher | |
| 4,460,555 A | 7/1984 | Thompson | |
| 4,556,063 A | 12/1985 | Thompson | |
| 4,562,751 A | 1/1986 | Nason | |
| 4,581,141 A | 4/1986 | Ash | |
| 4,650,587 A | 3/1987 | Polak | |
| 4,661,246 A * | 4/1987 | Ash | A61M 1/308 |
| | | | 210/257.2 |
| 4,678,408 A | 7/1987 | Mason | |
| 4,685,903 A | 8/1987 | Cable | |
| 4,747,822 A * | 5/1988 | Peabody | A61M 1/28 |
| | | | 128/DIG. 13 |
| 4,750,494 A | 6/1988 | King | |
| 4,772,560 A * | 9/1988 | Attar | G01N 33/526 |
| | | | 436/178 |
| 4,799,493 A | 1/1989 | DuFault | |
| 4,826,663 A | 5/1989 | Alberti | |
| 4,828,693 A | 5/1989 | Lindsay | |
| 4,950,230 A * | 8/1990 | Kendell | A61M 1/28 |
| | | | 604/32 |
| 4,976,683 A * | 12/1990 | Gauthier | A61M 1/287 |
| | | | 604/27 |
| 5,032,265 A | 7/1991 | Jha | |

| | | | |
|---|---|---|---|
| 5,080,653 A | 1/1992 | Voss | |
| 5,091,642 A * | 2/1992 | Chow | G01N 21/783 |
| | | | 356/402 |
| 5,092,838 A | 3/1992 | Faict | |
| 5,092,886 A | 3/1992 | Dobos-Hardy | |
| 5,097,122 A | 3/1992 | Coiman | |
| 5,127,404 A | 7/1992 | Wyborny | |
| 5,141,493 A | 8/1992 | Jacobsen | |
| 5,284,470 A | 2/1994 | Beltz | |
| 5,302,288 A | 4/1994 | Meidl | |
| 5,305,745 A | 4/1994 | Zacouto | |
| 5,312,547 A * | 5/1994 | Kruger | A61M 1/28 |
| | | | 210/317 |
| 5,318,750 A | 6/1994 | Lascombes | |
| 5,468,388 A | 11/1995 | Goddard | |
| 5,507,723 A | 4/1996 | Keshaviah | |
| 5,643,201 A | 7/1997 | Peabody | |
| 5,651,893 A | 7/1997 | Kenley | |
| 5,683,432 A | 11/1997 | Goedeke | |
| 5,744,031 A | 4/1998 | Bene | |
| 5,762,782 A | 6/1998 | Kenley | |
| 5,819,007 A | 10/1998 | Elghazzawi | |
| 5,902,336 A | 5/1999 | Mishkin | |
| 5,944,684 A | 8/1999 | Roberts | |
| 5,987,352 A | 11/1999 | Klein | |
| 6,042,721 A | 3/2000 | Peters | |
| 6,048,732 A | 4/2000 | Anslyn | |
| 6,052,622 A | 4/2000 | Holmstrom | |
| 6,058,331 A | 5/2000 | King | |
| 6,156,002 A | 12/2000 | Polaschegg | |
| 6,230,059 B1 | 5/2001 | Duffin | |
| 6,248,093 B1 | 6/2001 | Moberg | |
| 6,254,567 B1 | 7/2001 | Treu | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,505,075 B1 | 1/2003 | Weiner | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz | |
| 6,609,023 B1 | 8/2003 | Fischell | |
| 6,627,164 B1 | 9/2003 | Wong | |
| 6,645,191 B1 | 11/2003 | Knerr | |
| 6,676,608 B1 | 1/2004 | Keren | |
| 6,689,083 B1 | 2/2004 | Gelfand | |
| 6,706,007 B2 | 3/2004 | Gelfand | |
| 6,711,439 B1 | 3/2004 | Bradley | |
| 6,726,647 B1 | 4/2004 | Sternby | |
| 6,780,322 B1 | 8/2004 | Bissler | |
| 6,818,196 B2 | 11/2004 | Wong | |
| 6,878,283 B2 | 4/2005 | Thompson | |
| 6,887,214 B1 | 5/2005 | Levin | |
| 6,890,315 B1 | 5/2005 | Levin | |
| 6,960,179 B2 | 11/2005 | Gura | |
| 7,074,332 B2 | 7/2006 | Summerton | |
| 7,077,819 B1 | 7/2006 | Goldau | |
| 7,131,956 B1 | 11/2006 | Pirazzoli | |
| 7,175,809 B2 | 2/2007 | Gelfand | |
| 7,207,946 B2 | 4/2007 | Sirokman | |
| 7,208,092 B2 | 4/2007 | Micheli | |
| 7,276,042 B2 | 10/2007 | Polaschegg | |
| 7,399,289 B2 | 7/2008 | Gelfand | |
| 7,404,799 B1 | 7/2008 | Koh | |
| 7,500,958 B2 | 3/2009 | Asbrink | |
| 7,566,432 B2 | 7/2009 | Wong | |
| 7,575,564 B2 | 8/2009 | Childers | |
| 7,610,086 B1 | 10/2009 | Ke | |
| 7,674,231 B2 | 3/2010 | McCombie | |
| 7,704,361 B2 | 4/2010 | Garde | |
| 7,736,507 B2 | 6/2010 | Wong | |
| 7,744,553 B2 | 6/2010 | Kelly | |
| 7,754,852 B2 | 7/2010 | Burnett | |
| 7,756,572 B1 | 7/2010 | Fard | |
| 7,775,983 B2 | 8/2010 | Zhang | |
| 7,775,986 B2 | 8/2010 | Roeher | |
| 7,776,210 B2 | 8/2010 | Rosenbaum | |
| 7,785,463 B2 | 8/2010 | Bissler | |
| 7,794,141 B2 | 9/2010 | Perry | |

(56) References Cited

U.S. PATENT DOCUMENTS

| | | | |
|---|---|---|---|
| 7,850,635 | B2 | 12/2010 | Polaschegg |
| 7,857,976 | B2 | 12/2010 | Bissler |
| 7,867,214 | B2 | 1/2011 | Childers |
| 7,896,831 | B2 | 3/2011 | Sternby |
| 7,922,686 | B2 | 4/2011 | Childers |
| 7,922,911 | B2 | 4/2011 | Micheli |
| 7,947,179 | B2 | 5/2011 | Rosenbaum |
| 7,955,291 | B2 | 6/2011 | Sternby |
| 7,967,022 | B2 | 6/2011 | Grant |
| 7,981,082 | B2 | 7/2011 | Wang |
| 8,000,000 | B2 | 8/2011 | Greenberg |
| 8,034,161 | B2 | 10/2011 | Gura |
| 8,070,709 | B2 | 12/2011 | Childers |
| 8,096,969 | B2 | 1/2012 | Roberts |
| 8,105,260 | B2 | 1/2012 | Tonelli |
| 8,183,046 | B2 | 5/2012 | Lu |
| 8,187,250 | B2 | 5/2012 | Roberts |
| 8,197,439 | B2 | 6/2012 | Wang |
| 8,202,241 | B2 | 6/2012 | Karakama |
| 8,246,826 | B2 | 8/2012 | Wilt |
| 8,273,049 | B2 | 9/2012 | Demers |
| 8,282,828 | B2 | 10/2012 | Wallenas |
| 8,292,594 | B2 | 10/2012 | Tracey |
| 8,313,642 | B2 | 11/2012 | Yu |
| 8,317,492 | B2 | 11/2012 | Demers |
| 8,357,113 | B2 | 1/2013 | Childers |
| 8,366,316 | B2 | 2/2013 | Kamen |
| 8,366,655 | B2 | 2/2013 | Kamen |
| 8,404,091 | B2 | 3/2013 | Ding |
| 8,409,441 | B2 | 4/2013 | Wilt |
| 8,496,809 | B2 | 7/2013 | Roger |
| 8,499,780 | B2 | 8/2013 | Wilt |
| 8,500,676 | B2 | 8/2013 | Jansson |
| 8,512,271 | B2 | 8/2013 | Moissl |
| 8,518,260 | B2 | 8/2013 | Raimann |
| 8,521,482 | B2 | 8/2013 | Akonur |
| 8,535,525 | B2 | 9/2013 | Heyes |
| 8,560,510 | B2 | 10/2013 | Brueggerhoff |
| 8,580,112 | B2 | 11/2013 | Updyke |
| 8,597,227 | B2 | 12/2013 | Childers |
| 8,696,626 | B2 | 4/2014 | Kirsch |
| 8,815,095 | B2 * | 8/2014 | Micheli ............... A61M 1/1696 |
| | | | 210/637 |
| 8,903,492 | B2 | 12/2014 | Soykan |
| 8,926,542 | B2 | 1/2015 | Gerber |
| 9,700,663 | B2 | 7/2017 | Burbank |
| 9,907,897 | B2 * | 3/2018 | Burbank ............. A61M 1/1664 |
| 10,046,100 | B2 | 8/2018 | Burbank |
| 10,076,599 | B2 | 9/2018 | Eyrard |
| 10,076,735 | B2 | 9/2018 | Jansson |
| 10,173,881 | B2 | 1/2019 | Beavis |
| 10,459,459 | B2 | 10/2019 | Beavis |
| 10,478,544 | B2 | 11/2019 | Friederichs |
| 10,610,630 | B2 | 4/2020 | Burbank |
| 2002/0016550 | A1 | 2/2002 | Sweeney |
| 2002/0042561 | A1 | 4/2002 | Schulman |
| 2002/0112609 | A1 | 8/2002 | Wong |
| 2002/0162778 | A1 * | 11/2002 | Peabody ................. A61M 1/28 |
| | | | 210/85 |
| 2003/0028089 | A1 | 2/2003 | Galley |
| 2003/0069481 | A1 | 4/2003 | Hervy |
| 2003/0080059 | A1 | 5/2003 | Peterson |
| 2003/0097086 | A1 | 5/2003 | Gura |
| 2003/0105435 | A1 | 6/2003 | Taylor |
| 2003/0113931 | A1 | 6/2003 | Pan |
| 2003/0114787 | A1 | 6/2003 | Gura |
| 2003/0187479 | A1 | 10/2003 | Thong |
| 2004/0019312 | A1 | 1/2004 | Childers |
| 2004/0060865 | A1 * | 4/2004 | Callan .................... A61K 31/19 |
| | | | 210/646 |
| 2004/0068219 | A1 | 4/2004 | Summerton |
| 2004/0099593 | A1 | 5/2004 | DePaolis |
| 2004/0121982 | A1 * | 6/2004 | Martis ................. A61K 31/718 |
| | | | 514/58 |
| 2004/0147900 | A1 | 7/2004 | Polaschegg |
| 2004/0168969 | A1 | 9/2004 | Sternby |
| 2004/0215090 | A1 | 10/2004 | Erkkila |
| 2005/0065760 | A1 | 3/2005 | Murtfeldt |
| 2005/0113796 | A1 | 5/2005 | Taylor |
| 2005/0126961 | A1 | 6/2005 | Bissler |
| 2005/0126998 | A1 | 6/2005 | Childers |
| 2005/0131331 | A1 | 6/2005 | Kelly |
| 2005/0150832 | A1 | 7/2005 | Tsukamoto |
| 2005/0214863 | A1 | 9/2005 | McDevitt |
| 2005/0234354 | A1 | 10/2005 | Rowlandson |
| 2005/0234357 | A1 | 10/2005 | Xue |
| 2005/0234381 | A1 | 10/2005 | Niemetz |
| 2005/0234534 | A1 | 10/2005 | Rowlandson |
| 2005/0236330 | A1 | 10/2005 | Nier |
| 2005/0265895 | A1 | 12/2005 | Kopelman |
| 2005/0274658 | A1 | 12/2005 | Rosenbaum |
| 2006/0025661 | A1 | 2/2006 | Sweeney |
| 2006/0025748 | A1 | 2/2006 | Ye |
| 2006/0058731 | A1 | 3/2006 | Burnett |
| 2006/0191850 | A1 | 8/2006 | Bosetto |
| 2006/0195064 | A1 | 8/2006 | Plahey |
| 2006/0217771 | A1 | 9/2006 | Soykan |
| 2006/0226079 | A1 | 10/2006 | Mori |
| 2006/0241709 | A1 | 10/2006 | Soykan |
| 2006/0247548 | A1 | 11/2006 | Sarkar |
| 2006/0264894 | A1 | 11/2006 | Moberg |
| 2007/0007208 | A1 | 1/2007 | Brugger |
| 2007/0038138 | A1 | 2/2007 | Gill |
| 2007/0066928 | A1 | 3/2007 | Lannoy |
| 2007/0073168 | A1 | 3/2007 | Zhang |
| 2007/0138011 | A1 | 6/2007 | Hofmann |
| 2007/0161113 | A1 | 7/2007 | Ash |
| 2007/0175827 | A1 | 8/2007 | Wariar |
| 2007/0179431 | A1 | 8/2007 | Roberts |
| 2007/0213653 | A1 | 9/2007 | Childers |
| 2007/0215545 | A1 | 9/2007 | Bissler |
| 2007/0255250 | A1 | 11/2007 | Moberg |
| 2007/0276270 | A1 | 11/2007 | Tran |
| 2008/0006570 | A1 | 1/2008 | Gura |
| 2008/0021337 | A1 | 1/2008 | Li |
| 2008/0053905 | A9 | 3/2008 | Brugger |
| 2008/0067132 | A1 | 3/2008 | Ross |
| 2008/0093276 | A1 | 4/2008 | Roger |
| 2008/0200866 | A1 | 8/2008 | Prisco |
| 2008/0215247 | A1 | 9/2008 | Tonelli |
| 2008/0253427 | A1 | 10/2008 | Kamen |
| 2009/0020471 | A1 | 1/2009 | Tsukamoto |
| 2009/0036825 | A1 | 2/2009 | Petersen |
| 2009/0101577 | A1 | 4/2009 | Fulkerson |
| 2009/0124869 | A1 | 5/2009 | Hu |
| 2009/0124963 | A1 | 5/2009 | Hogard |
| 2009/0127193 | A1 | 5/2009 | Updyke |
| 2009/0149776 | A1 | 6/2009 | Adams |
| 2009/0171261 | A1 | 7/2009 | Sternby |
| 2009/0264776 | A1 | 10/2009 | Vardy |
| 2009/0275849 | A1 | 11/2009 | Stewart |
| 2009/0275883 | A1 | 11/2009 | Chapman |
| 2009/0281484 | A1 | 11/2009 | Childers |
| 2009/0282980 | A1 | 11/2009 | Gura |
| 2009/0314063 | A1 | 12/2009 | Sternby |
| 2010/0004588 | A1 | 1/2010 | Yeh |
| 2010/0010425 | A1 | 1/2010 | Yu |
| 2010/0010429 | A1 | 1/2010 | Childers |
| 2010/0042035 | A1 | 2/2010 | Moissl |
| 2010/0076398 | A1 | 3/2010 | Scheurer |
| 2010/0078381 | A1 | 4/2010 | Merchant |
| 2010/0078387 | A1 | 4/2010 | Wong |
| 2010/0084330 | A1 | 4/2010 | Wong |
| 2010/0087771 | A1 | 4/2010 | Karakama |
| 2010/0094158 | A1 | 4/2010 | Solem |
| 2010/0113891 | A1 | 5/2010 | Barrett |
| 2010/0114012 | A1 | 5/2010 | Sandford |
| 2010/0137693 | A1 | 6/2010 | Porras |
| 2010/0137782 | A1 | 6/2010 | Jansson |
| 2010/0168546 | A1 | 7/2010 | Kamath |
| 2010/0217180 | A1 | 8/2010 | Akonur |
| 2010/0217181 | A1 | 8/2010 | Roberts |
| 2010/0224492 | A1 | 9/2010 | Ding |
| 2010/0234795 | A1 | 9/2010 | Wallenas |

(56) References Cited

U.S. PATENT DOCUMENTS

| | | |
|---|---|---|
| 2010/0241045 A1 | 9/2010 | Kelly |
| 2010/0264086 A1 | 10/2010 | Noack |
| 2010/0312172 A1* | 12/2010 | Hoffman ............ A61M 1/1696 604/28 |
| 2010/0312174 A1* | 12/2010 | Hoffman ............ A61M 1/155 604/29 |
| 2011/0017665 A1 | 1/2011 | Updyke |
| 2011/0048949 A1 | 3/2011 | Ding et al. |
| 2011/0066006 A1 | 3/2011 | Banet |
| 2011/0066043 A1 | 3/2011 | Banet |
| 2011/0071465 A1 | 3/2011 | Wang |
| 2011/0077574 A1 | 3/2011 | Sigg |
| 2011/0077575 A1 | 3/2011 | Kraemer |
| 2011/0079558 A1 | 4/2011 | Raimann |
| 2011/0081728 A1 | 4/2011 | Putnam |
| 2011/0087187 A1 | 4/2011 | Beck |
| 2011/0100909 A1 | 5/2011 | Stange |
| 2011/0106003 A1 | 5/2011 | Childers |
| 2011/0130666 A1 | 6/2011 | Dong |
| 2011/0137136 A1 | 6/2011 | Kotanko |
| 2011/0141116 A1 | 6/2011 | Dalesch |
| 2011/0144570 A1 | 6/2011 | Childers |
| 2011/0184340 A1 | 7/2011 | Tan |
| 2011/0208105 A1 | 8/2011 | Brandl |
| 2011/0272337 A1 | 11/2011 | Palmer |
| 2011/0301447 A1 | 12/2011 | Park |
| 2011/0301472 A1 | 12/2011 | Grober |
| 2012/0016228 A1 | 1/2012 | Kroh |
| 2012/0029937 A1 | 2/2012 | Neftel |
| 2012/0083729 A1 | 4/2012 | Childers |
| 2012/0085707 A1 | 4/2012 | Beiriger |
| 2012/0115248 A1 | 5/2012 | Ansyln |
| 2012/0135396 A1 | 5/2012 | McDevitt |
| 2012/0181230 A1 | 7/2012 | Kloeffel |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0283581 A1 | 11/2012 | Olde et al. |
| 2012/0303079 A1 | 11/2012 | Mahajan |
| 2013/0037465 A1 | 2/2013 | Heyes |
| 2013/0062265 A1 | 3/2013 | Balschat |
| 2013/0116578 A1 | 5/2013 | An |
| 2013/0168316 A1 | 7/2013 | Noguchi |
| 2013/0186759 A1 | 7/2013 | Lin |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0276375 A1* | 9/2014 | Minkus ................. A61M 1/284 604/28 |
| 2014/0314625 A1 | 10/2014 | Clift |
| 2015/0032023 A1 | 1/2015 | Soykan |
| 2015/0080682 A1 | 3/2015 | Gerber |
| 2015/0088047 A1 | 3/2015 | Gerber |
| 2015/0144539 A1 | 5/2015 | Pudil |
| 2015/0148697 A1 | 5/2015 | Burnes |
| 2015/0149096 A1 | 5/2015 | Soykan |
| 2015/0250427 A1 | 9/2015 | Soykan |
| 2015/0343126 A1 | 12/2015 | Merchant |
| 2015/0352269 A1 | 12/2015 | Gerber |
| 2015/0367054 A1 | 12/2015 | Gerber |
| 2016/0023467 A1 | 1/2016 | Din et al. |
| 2016/0143774 A1 | 5/2016 | Burnett |
| 2016/0166753 A1 | 6/2016 | Meyer |
| 2016/0206801 A1 | 7/2016 | Gerber |
| 2016/0331884 A1 | 11/2016 | Sigg |
| 2017/0319768 A1 | 11/2017 | Szpara |
| 2018/0043080 A1 | 2/2018 | Gerber |
| 2018/0221555 A1 | 8/2018 | Rohde |
| 2019/0125952 A1 | 5/2019 | Jansson |
| 2019/0125954 A1 | 5/2019 | Mathiot |
| 2019/0151526 A1 | 5/2019 | Wieslander |
| 2019/0240389 A1 | 8/2019 | Rohde |

FOREIGN PATENT DOCUMENTS

| | | |
|---|---|---|
| CN | 101193667 | 6/2008 |
| CN | 101300476 A | 11/2008 |
| CN | 201342127 | 11/2009 |
| CN | 202048893 | 3/2011 |
| CN | 103037917 | 4/2013 |
| CN | 103394139 | 11/2013 |
| CN | 103619372 | 3/2014 |
| CN | 103751871 | 4/2014 |
| CN | 104174077 | 12/2014 |
| CN | 104833635 A | 8/2015 |
| CN | 104884102 | 9/2015 |
| CN | 105008893 B | 10/2015 |
| CN | 105142692 | 12/2015 |
| CN | 105692957 A | 6/2016 |
| CN | 205672288 | 11/2016 |
| CN | 107206147 | 9/2017 |
| DE | 3224823 | 1/1984 |
| DE | 102006028172 A1 | 12/2017 |
| EP | 266795 A2 | 11/1987 |
| EP | 0402505 | 12/1990 |
| EP | 0272414 | 10/1991 |
| EP | 0330892 | 7/1994 |
| EP | 1124599 | 5/2000 |
| EP | 1175238 | 11/2000 |
| EP | 1281351 | 2/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1345856 B1 | 3/2013 |

(56) References Cited

FOREIGN PATENT DOCUMENTS

| | | | |
|---|---|---|---|
| EP | 2344220 B1 | 4/2013 | |
| EP | 1351756 | 7/2013 | |
| EP | 2190498 | 7/2013 | |
| EP | 2701596 | 3/2014 | |
| EP | 1582226 | 1/2016 | |
| JP | S551980138462 | 10/1980 | |
| JP | S63-143077 | 11/1987 | |
| JP | 2002533170 | 10/2002 | |
| JP | 2002542900 | 12/2002 | |
| JP | 2003235965 | 8/2003 | |
| JP | 2005-533573 | 11/2005 | |
| JP | 5099464 | 10/2012 | |
| WO | WO1992005814 | 4/1992 | |
| WO | 1995003839 | 2/1995 | |
| WO | WO 1998054563 | 12/1998 | |
| WO | WO1999006082 | 2/1999 | |
| WO | 9937342 | 7/1999 | |
| WO | 0057935 | 10/2000 | |
| WO | WO-0057935 A1 * | 10/2000 | ........... A61L 2/0023 |
| WO | WO2000057935 A1 | 10/2000 | |
| WO | 200066197 A1 | 11/2000 | |
| WO | 2000066197 | 11/2000 | |
| WO | 200170307 A1 | 9/2001 | |
| WO | 2001085295 A2 | 9/2001 | |
| WO | 0185295 A2 | 11/2001 | |
| WO | 1085295 | 11/2001 | |
| WO | 2002013691 | 2/2002 | |
| WO | WO 20020053211 | 7/2002 | |
| WO | 2003043677 A2 | 5/2003 | |
| WO | 2003043680 | 5/2003 | |
| WO | 2003051422 A2 | 6/2003 | |
| WO | 2004008826 | 1/2004 | |
| WO | 2004009156 | 1/2004 | |
| WO | 2004009158 | 1/2004 | |
| WO | 2004030716 A2 | 4/2004 | |
| WO | 2004030717 A2 | 4/2004 | |
| WO | 2004064616 A2 | 8/2004 | |
| WO | 2005033701 | 4/2005 | |
| WO | 2005061026 | 7/2005 | |
| WO | 2005123230 A2 | 12/2005 | |
| WO | 2006011009 | 2/2006 | |
| WO | 2006017446 | 2/2006 | |
| WO | 2007038347 | 4/2007 | |
| WO | 2007089855 A2 | 8/2007 | |
| WO | WO2009094035 A1 | 1/2008 | |
| WO | 2008037410 | 4/2008 | |
| WO | 2009026603 | 12/2008 | |
| WO | 2009024566 | 2/2009 | |
| WO | 2009026603 A1 | 3/2009 | |
| WO | 2009061608 | 5/2009 | |
| WO | 2009094184 | 7/2009 | |
| WO | 2009157877 A1 | 12/2009 | |
| WO | 2009157878 A1 | 12/2009 | |
| WO | WO2009154955 A2 | 12/2009 | |
| WO | WO 20090154955 | 12/2009 | |
| WO | WO 20100002830 | 1/2010 | |
| WO | 2010024963 | 3/2010 | |
| WO | 2010028860 | 3/2010 | |
| WO | 2010028860 A1 | 3/2010 | |
| WO | 2010033314 | 3/2010 | |
| WO | 2010033699 | 3/2010 | |
| WO | 2010077851 | 7/2010 | |
| WO | 2010096659 | 10/2010 | |
| WO | 2010121820 | 10/2010 | |
| WO | 2011025705 A1 | 3/2011 | |
| WO | 2011026645 | 3/2011 | |
| WO | WO2013022760 A1 | 8/2011 | |
| WO | WO 2011/132046 | 10/2011 | |
| WO | 2011137693 | 11/2011 | |
| WO | WO2011161056 | 12/2011 | |
| WO | 2012042323 | 4/2012 | |
| WO | 2012050781 | 4/2012 | |
| WO | 2012051996 | 4/2012 | |
| WO | 2012073420 | 7/2012 | |
| WO | WO 2012/129501 | 9/2012 | |
| WO | 2012148781 | 11/2012 | |
| WO | 2012148786 | 11/2012 | |
| WO | 2012148787 A1 | 11/2012 | |
| WO | 2012148789 | 11/2012 | |
| WO | 2012162515 A2 | 11/2012 | |
| WO | 20120277551 | 11/2012 | |
| WO | WO2012148788 A1 | 11/2012 | |
| WO | WO 20120148784 | 11/2012 | |
| WO | 2012148784 | 12/2012 | |
| WO | 2012172398 | 12/2012 | |
| WO | 2013019179 A1 | 2/2013 | |
| WO | 2013019994 A2 | 2/2013 | |
| WO | 2013025844 | 2/2013 | |
| WO | 2013028809 A3 | 2/2013 | |
| WO | 2013101292 | 7/2013 | |
| WO | 2013103607 A1 | 7/2013 | |
| WO | 2013103906 | 7/2013 | |
| WO | 2013110906 | 8/2013 | |
| WO | 2013110919 | 8/2013 | |
| WO | 2013114063 A1 | 8/2013 | |
| WO | 2013121162 A1 | 8/2013 | |
| WO | 2013140346 | 9/2013 | |
| WO | 2013141896 | 9/2013 | |
| WO | 2013101292 A3 | 10/2013 | |
| WO | 14066254 | 5/2014 | |
| WO | 14066255 | 5/2014 | |
| WO | 14077082 | 5/2014 | |
| WO | 2014121162 | 8/2014 | |
| WO | 2014121163 | 8/2014 | |
| WO | 2014121167 | 8/2014 | |
| WO | 2014121169 | 8/2014 | |
| WO | WO2014121161 | 8/2014 | |
| WO | WO 20140121161 | 8/2014 | |
| WO | WO 20140121169 | 8/2014 | |
| WO | WO2015081221 A1 | 6/2015 | |
| WO | WO 20150130205 | 9/2015 | |
| WO | WO 20150159280 | 10/2015 | |
| WO | WO 20160080883 | 5/2016 | |
| WO | WO 20170034452 | 3/2017 | |
| WO | WO 2017/176687 | 10/2017 | |
| WO | WO 2017/176701 | 10/2017 | |

OTHER PUBLICATIONS

Dejardin, et al, Intraperitoneal pressure in PD patients: relationship to intraperitoneal volume, body size and PD-related complications, Nephrol Dial Transplant. May 2007;22(5):1437-44.

[NPL105] Brynda, et. al., The detection of toman 2-microglobuiin by grating coupler immunosensor with three dimensional antibody networks. Biosensors & Bioelectronics, 1999, 363-368, 14(4).

[NPL10] Wheaton, et al., Dowex Ion Exchange Resins— Fundamentals of Ion Exchange; Jun. 2000, pp. 1-9. http://www.dow.com/scripts/litorder.asp?filepath=liquidseps/pdfs/noreg/177-01837.pdf.

[NPL111] Zhong, et. al., Miniature urea sensor based on H(+)-ion sensitive field effect transistor and its application in clinical analysis, Chin. J. Biotechnol., 1992, 57-65. 8(1).

[NPL119] PCT/US2012/034331, International Search Report and Written Opinion dated Jul. 9, 2012.

[NPL121] Roberts M, The regenerative dialysis (REDY) sorbent system. Nephrology, 1998, 275-278:4.

[NPL138] U.S. Appl. No. 61/480,544.

[NPL139] U.S. Appl. No. 61/480,541 dated Apr. 29, 2011.

[NPL142] Hemametrics, Crit-Line Hematocrit Accuracy, 2003, 1-5, vol. 1, Tech Note No. 11 (Rev. D).

[NPL144] Weissman, S., et al., Hydroxyurea-induced hepatitis in human immunodeficiency virus-positive patients. Clin. Infec. Dis, (Jul. 29, 1999): 223-224.

[NPL146] PCT/US2012/034334, International Search Report, Jul. 6, 2012.

[NPL147] PCT/US2012/034335, International Search Report, Sep. 5, 2012.

[NPL148] PCT/US/2012/034327, International Search Report, Aug. 13, 2013.

[NPL149] PCT/US/2012/034329, International Search Report, Dec. 3, 2012.

(56)         References Cited

OTHER PUBLICATIONS

[NPL14] Foley, et al., Long Interdialytic Interval and Martality among Patients Receiving Hemodialysis, N Engl Jrnl Med. 2011:365(12):1099-1107.

[NPL15] PCT International Search Report from International Application No. PCT/US2014/067650, dated Nov. 27, 2013.

[NPL169] Wang, Fundamentals of intrathoracic impedance monitoring in heart failure, Am. J. Cardiology, 2007, 3G-10G: Suppl.

[NPL16] PCT/US2014/067650 International Search Report Written Opinion mailed Mar. 9, 2015.

[NPL170] Bleyer, et al, Kidney International. Jun. 2006; 69(12):2268-2273.

[NPL176] Bleyer, et. al., Sudden and cardiac death rated in hemodialysis patients, Kidney International. 1999, 1553-1559: 55.

[NPL180] PCT/US2012/034335, International Preliminary Report on Patentability, Nov. 7, 2013.

[NPL181] PCT/US2012/034303, Internationa Search Report, Jul. 6, 2013.

[NPL186] PCT/US2012/034332, Internatonal Preliminary Report on Patentability, Oct. 29, 2013.

[NPL187] PCT/US2012/034333, International Preliminary Report on Patentability, Oct. 29, 2013.

[NPL188] PCT/US2012/034333, International Search Report, Aug. 29, 2012.

[NPL188] PCT/US2012/034333, International Search Report, Aug. 29, 2013.

[NPL195] PCT/US2012/034327, International Preliminary Report on Patentability, Oct. 29, 2013.

[NPL197] PCT/US2012/034330, International Preliminary Report on Patentability, Oct. 29, 2013.

[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

[NPL217] U.S. Appl. No. 13/757,722, filed Feb. 1, 2013.

[NPL218] U.S. Appl. No. 13/757,794, filed Feb. 2, 2012.

[NPL219] U.S. Appl. No. 13/791,755, filed Mar. 8, 2013.

[NPL21] U.S. Appl. No. 13/424,479 dated Nov. 1, 2012.

[NPL220] U.S. Appl. No. 13/757,792, filed Feb. 2, 2013.

[NPL222] U.S. Appl. No. 13/757,794, filed Feb. 2, 2013.

[NPL227] U.S. Appl. No. 13/837,287, filed Mar. 15, 2013.

[NPL22] U.S. Appl. No. 13/424,429 dated Nov. 1, 2012.

[NPL230] Redfield, et. al, Restoration of renal response to atrial natriuretic factor in experimental low-output heat failure, Am. J. Physiol., Oct. 1, 1989, R917-923:257.

[NPL231] Rogoza, et. al., Validation of A&D UA-767 device for the self-measurement of blood pressure, Blood Pressure Monitoring, 2000, 227-231, 5(4).

[NPL233] PCT/US2012/034329, International Preliminary Report on Patentability, Oct. 29, 2013.

[NPL234] Lima, et. al., An electrochemical sensor based on nanostructure hollandite-type manganese oxide for detection of potassium ion, Sensors, Aug. 24, 2009, 6613-8625, 9.

[NPL235] MacLean, et, al., Effects of hindlimb contraction on pressor and muscle interstitial metabolite responses in the cat, J. App. Physiol., 1998, 1583-1592, 85(4).

[NPL237] U.S. Appl. No. 13/757,693, dated Feb. 1, 2013.

[NPL238] PCT Application, PCT/US20013/020404, filed Jan. 4, 2013.

[NPL23] U.S. Appl. No. 13/424,525.

[NPL240] U.S. Appl. No. 13/836,973, filed Mar. 15, 2013.

[NPL241] U.S. Appl. No. 14/259,655, filed Apr. 23, 2014.

[NPL242] U.S. Appl. No. 14/259,589, filed Apr. 23, 2014.

[NPL264] PCT/US2014/014357 International Search Report and Written Opinion dated May 19, 2014.

[NPL264] PCT/US2014/014357 International Search Report and Written Opinion mailed May 19, 2014.

[NPL268] Ronco et al. 2008, Cardiorenal Syndrome, Journal American College Cardiology, 52:1527-1539, Abstract.

[NPL26] Overgaard, et. al., Activity-induced recovery of excitability in K+-depressed rat soleus muscle, Am. J. P 280: R48-R55, Jan. 1, 2001.

[NPL27] Overgaard. et. al., Relations between excitability and contractility in rate soleusmuscle: role of the NA+-K+ pump and NA+-K-S gradients. Journal of Physiology, 1999, 215-225, 518(1).

[NPL285] Zoccali, Pulmonary Congestion Predicts Cardiac Events and Mortality in ESRD, Clinical Epidemiology, J. Am Soc Nephrol 24:639-646, 2013.

[NPL306] Coast, et al. 1990, An approach to Cardiac Arrhythmia analysis Using Hidden Markov Models, IEEE Transactions on Biomedical Engineering. 1990, 37(9):826-835.

[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.

[NPL310] U.S. Appl. No. 61/480,532.

[NPL311] U.S. Appl. No. 13/424,479.

[NPL312] U.S. Appl. No. 13/424,429 dated Nov. 1, 2012.

[NPL313] U.S. Appl. No. 13/424,525.

[NPL317] U.S. Appl. No. 61/480,530.

[NPL318] U.S. Appl. No. 61/480,528 dated Apr. 29, 2011.

[NPL322] Velasco, Optimal Fluid Control can Normalize Cardiovascular Risk Markers and Limit Left Ventricular Hypertrophy in Thrice Weekly Dialysis Patients, Hemodialysis Intenational, 16:465-472, 2012.

[NPL323] Whitman, CKD and Sudden Cardiac Death: Epidemiology, Mechanisms, and Therapeutic Approaches, J Am Soc Nephrol, 23:1929-1939, 2012.

[NPL324] Hall, Hospitalization for Congestive Heart Failure: United States, 2000-2010, NCHS Data Brief, No. 108, Oct. 2012.

[NPL325] Albert, Fluid Management Strategies in Heart Failure, Critical Care Nurse, 32:20-32, 2012.

[NPL326] PCT/US2014/065201 International Search Report mailed May 26, 2015.

[NPL328] Genovesi, et al., Nephrology, Dialysis, Transplantation 2009; 24(8):2529-2536.

[NPL32] Secemsky, et. al, High prevalence of cardiac autonomic dysfunction and T-wave alternans in dialysis patients. Heart Rhythm, Apr. 2011, 592-598 : vol. 8, No. 4.

[NPL339] U.S. Appl. No. 13/424,517 IDS, filed Aug. 2, 2012.

[NPL340] U.S. Appl. No. 13/424,517, IDS filed Dec. 2, 2013.

[NPL35] Wei, et. al., Fullerene-cryptand coated piezoelectric crystal urea sensor based on urease, Analytica Chimica Acta, 2001,77-85:437.

[NPL376] Gambro AK 96 Dialysis Machine Operators Manual, Dec. 2012. p. 1-140.

[NPL376] Gambro AK 96 Dialysis Machine Operators Manual, Dec. 2012. p. 141-280.

[NPL376] Gambro AK 96 Dialysis Machine Operators Manual, Dec. 2012. p. 281-420.

[NPL376] Gambro AK 96 Dialysis Machine Operators Manual, Dec. 2012. p. 421-534.

[NPL37] U.S. Appl. No. 13/368,225 dated Feb. 7, 2012.

[NPL383] Leifer et al., A Study on the Temperature Variation of Rise Velocity for Large Clean Bubbles, J. Atmospheric & Oceanic Tech., vol. 17, pp. 1392-1402, Oct. 2000.

[NPL384] Talaia, Terminal Velocity of a Bubble Rise in a Liquid Column, World Acad. of Sci., Engineering & Tech., vol. 28, pp. 264-268, Published Jan. 1, 2007.

[NPL386] The FHN Trial Group. In-Center. Hemodialysis Six Times per Week versus Three Times per Week, New England Journal of Medicine, 2010 Abstract.

[NPL39] PCT/US2012/034332, International Search Report, Jul. 5, 2012.

[NPL46] Siegenthaler, et al., Pulmonary fluid status monitoring with intrathoracic impedance, Journal of Clinical Monitoring and Computing, 24:449-451, published Jan. 12, 2011.

[NPL477] Office Action in U.S. Appl. No. 13/757,792 Dated Apr. 6, 2015.

[NPL47] U.S. Appl. No. 61/480,544.

[NPL483] Office Action in U.S. Appl. No. 13/424,525 dated Aug. 11, 2015.

(56) References Cited

OTHER PUBLICATIONS

[NPL486] Office Action in U.S. Appl. No. 13/424,525 dated Oct. 20, 2016.
[NPL494] John Wm Agar: Review: Understanding sorbent dialysis systems, Nephrology, vol. 15, No. 4, Jun. 1, 2010, pp. 406-411.
[NPL495] European Office Action in Application 12717020.7 dated Sep. 14, 2016.
[NPL500] Office Action in U.S. Appl. No. 14/554,272 Dated Aug. 8, 2016.
[NPL501] Office Action in U.S. Appl. No. 13/424,467 Dated Oct. 16, 2013.
[NPL502] Office Action in U.S. Appl. No. 13/424,467 Dated Mar. 3, 2014.
[NPL503] Office Action in U.S. Appl. No. 13/424,490 Dated Oct. 22, 2013.
[NPL504] Office Action in U.S. Appl. No. 13/424,490 Dated Mar. 10, 2014.
[NPL505] Office Action in U.S. Appl. No. 13/424,490 Dated Jul. 14, 2014.
[NPL506] Office Action in U.S. Appl. No. 13/424,490 Dated Dec. 5, 2014.
[NPL507] Office Action in U.S. Appl. No. 13/424,525 dated Sep. 29, 2014.
[NPL508] Office Action in U.S. Appl. No. 13/424,525 dated May 6, 2015.
[NPL509] Office Action in U.S. Appl. No. 13/424,454 Dated Oct. 17, 2013.
[NPL510] Office Action in U.S. Appl. No. 13/424,454 Dated Mar. 10, 2014.
[NPL511] Office action in U.S. Appl. No. 13/424,429 dated Oct. 15, 2015.
[NPL512] Office Action in U.S. Appl. No. 12/571,127 dated Feb. 27, 2014.
[NPL513] Office Action in U.S. Appl. No. 12/571,127 dated Jul. 6, 2015.
[NPL514] Office Action in U.S. Appl. No. 12/571,127 dated Dec. 17, 2015.
[NPL521] Office Action in U.S. Appl. No. 14/554,338 Dated Jun. 7, 2016.
[NPL522] Office Action in U.S. Appl. No. 14/554,338 Dated Sep. 28, 2016.
[NPL524] Office Action in U.S. Appl. No. 13/424,429 Dated Oct. 15, 2015.
[NPL525] Office Action in U.S. Appl. No. 12/571,127 dated Feb. 27, 2014.
[NPL526] Office Action in U.S. Appl. No. 12/571,127 dated Jul. 6, 2015.
[NPL527] Office Action in U.S. Appl. No. 12/571,127 dated Dec. 17, 2015.
[NPL539] Office Action in U.S. Appl. No. 12/571,127 dated Nov. 8, 2012.
[NPL540] Office Action in U.S. Appl. No. 14/554,338 Dated Jun. 7, 2016.
[NPL541] Office Action in U.S. Appl. No. 14/554,338 Dated Sep. 28, 2016.
[NPL542] Office Action in U.S. Appl. No. 14/554,272 Dated Aug. 8, 2016.
[NPL543] Office Action in U.S. Appl. No. 13/424,479 Dated Oct. 25, 2014.
[NPL545] Office Action in U.S. Appl. No. 14/566,686 Dated Apr. 28, 2016.
[NPL547] Office Action in Chinese Application No. 201510511657.9 Dated Dec. 28, 2016.
[NPL55] U.S. Appl. No. 13/424,454.
[NPL57] U.S. Appl. No. 13/424,467.
[NPL582] Office Action in U.S. Appl. No. 13/757,792 dated Apr. 6, 2015.
[NPL62] U.S. Appl. No. 13/424,533.
[NPL632] Lakerveld et al, Primary prevention of diabetes mellitus type 2 and cardiovascular diseases using a cognitive behavior program aimed at lifestyle changes in people at risk: Design of a randomized controlled trial, 2008, BMC Endocrine Disorders, 8(6): 1-19.
[NPL633] Gordhandas et al, Real-Time Extraction and Analysis of Key Morphological Features in the Electrocardiogram, for Data Compression and Clinical Decision Support, 2004, Computational Physiology, pp. 15-18.
[NPL671] European Office Action in Application 12717020.7 dated Dec. 11, 2015.
[NPL672] PCT/US2012/034331 International Preliminary Report on Patentability and Written Opinion dated Oct. 29, 2013.
[NPL674] Office Action in Chinese Application No. 201280020932.1 Dated Jan. 7, 2015.
[NPL675] Office Action in Chinese Application No. 201280020932.1 Dated Apr. 3, 2015.
[NPL67] U.S. Appl. No. 13/424,490.
[NPL68] U.S. Appl. No. 13/424,517.
[NPL693] PCT/US2012/034330, International Search Report and Written Opinion dated Aug. 28, 2012.
[NPL699] Office Action in Chinese Application No. 201280020937.4 dated Oct. 22, 2016.
[NPL700] Office Action in Japanese Application No. 2014-508434 dated Nov. 16, 2015.
[NPL701] Office Action in Japanese Application No. 2014-508434 dated Dec. 8, 2014.
[NPL702] Office Action in Japanese Application No. 2014-508434 dated Nov. 4, 2016.
[NPL703] Office Action in European Application No. 12717019.9 dated Feb. 16, 2017.
[NPL706] Office Action in Chinese Application No. 201510511657.9 dated May 10, 2017.
[NPL709] PCT/US2014/065201 International Preliminary Report on Patentability mailed May 19, 2016.
[NPL727] Office Action in European Application No. EP 12717021.5 dated Feb. 3, 2017.
[NPL735] Office Action in Chinese Application No. 201510593695.3 dated Jul. 12, 2017.
[NPL748] Office Action in European Application No. EP 12719170.8 dated Jan. 14, 2015.
[NPL749] Office Action in Japanese Application No. JP 2014-508437 dated Dec. 8, 2014.
[NPL757] U.S. Appl. No. 60/650,497 dated Feb. 7, 2005.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, Jun. 12, 2017.
[NPL] European Search Report for Application No. 14865128.4 dated Jun. 20, 2017.
[NPL] Green et al., Sudden Cardiac Death in Hemodialysis Patients: an In-Depth Review , Am J Kidney Dis 57(6)921:929.
[NPL] Rajan et al. Generalized Feature Extraction for Time-Varying Autoregressive Models, IEEE Transacion Signal Processing vol. 44, No. 10.
Castellanos, et al, Clinical Relevance of Intraperitoneal Pressure in Peritoneal Dialysis Patients, Perit Dial Int. Sep.-Oct. 2017;37(5):562-567. doi: 10.3747/pdi.2016.00267. Epub Jul. 11, 2017.
Chinese OA in 201710669452.2 of Oct. 16, 2019.
Chinese Office Action for App. No. 201710669451.8, dated Sep. 12, 2019.
Chinese Office Action for App. No. 201710669452.2, dated Dec. 3, 2019.
Chinese Office Action for App. No. 2019071601874110, dated Jul. 19, 2019.
Chinese Office Action in App. No. 201480059332.5, Dated Mar. 30, 2018.
European Search Report for App. No. 17185636.2, Dated Mar. 27, 2018.
European Search Report for App. No. 14859115.9, dated Jan. 5, 2018.
European Search Report for App. No. 17185636.2 dated Jan. 10, 2018.

(56)     References Cited

OTHER PUBLICATIONS

European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.
European Search Report for App. No. 17190053.3, dated Jan. 2, 2018.
European Search Report for App. No. 17190066, dated Jan. 16, 2018.
European Search Report for App. No. 17190084, dated Feb. 9, 2018.
Henderson, et al, "Online Preparation of Sterile Pyrogen-Free Electrolyte Solution," Trans. Am. Soc. Artif.Intern.Organs, 1978 pp. 465-467.
Indian OA of Nov. 21, 2019 in 2981/KOLNP/2013.
International Preliminary Report on Patentability for App. No. PCT/US2019/019334, dated Jun. 12, 2019.
Laurent, Jeanpierre, "Continuous Monitoring of Dynamic Systems: Application to Monitoring of Dialyzed Patients" Oct. 30, 2004, received from internet: http://laurent.jeanpierre 1.free.fr/recherche/papiers/aista2004.pdf.
Office Action in Chinese App. No. 201710778666.3 dated Sep. 19, 2019.
PCT/US2016/058579 International Search Report dated Jan. 31, 2017.
PCT/US2016/058579_WO.
PCT/US2017/025868 International Search Report dated Jun. 29, 2017.
PCT/US2017/025868 Written Opinion dated Jun. 29, 2017.
PCT/US2017/030377_ISR.

PCT/US2017/030377_WO.
PCTUS20170146199 ISR and written opinion, Feb. 19, 2018.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
Written Opinion in Dutch App. No. 2018577, dated Nov. 2, 2017.
Office Action for European App. No. 17718241.7, dated Apr. 2, 2020.
Chinese Office Action for App. No. 201780019362.7, dated Jun. 2, 2020.
Chinese Office Action for App. No. 201780019237.6, dated May 25, 2020.
Chinese Office Action for App. No. 201780019238.0, dated May 7, 2020.
Chinese Office Action for App. No. 201811107614.4, dated Sep. 28, 2020.
Office Action in Chinese App. No. 201780019238.0, dated Sep. 25, 2020.
Chinese Office Action for App. No. 201811155891.2, dated Oct. 10, 2020.
AU Examiners Report for Application No. 2017246829, dated Jan. 9, 2021.
Chinese Office Action for App. No. 201780019237.6, dated Feb. 1, 2021.

\* cited by examiner

PERITONEAL DIALYSATE FLUID GENERATION SYSTEM

CROSS-REFERENCE TO RELATED APPLICATION

This application is a Continuation of U.S. patent application Ser. No. 15/478,562 filed Apr. 4, 2017, which claims the benefit of and priority to U.S. Provisional Patent Application No. 62/318,169 filed Apr. 4, 2016, the entire disclosure of which is incorporated by reference herein.

FIELD OF THE INVENTION

The invention relates to devices, systems, and methods for generating a peritoneal dialysate having purity and sterility characteristics suitable for Peritoneal Dialysis (PD). The peritoneal dialysate can be generated from water of variable quality using a dialysate generation flow path containing a sterilization module. The sterilization module can be any one or more of an ultrafilter, Ultraviolet (UV) light source, microbial filter, dialyzer, and combinations thereof. Peritoneal dialysate generation system and related methods are described that can automatically generate peritoneal dialysate fluid.

BACKGROUND

Peritoneal Dialysis (PD), including Automated Peritoneal Dialysis (APD) and Continuous Ambulatory Peritoneal Dialysis (CAPD), is a dialysis treatment that can be performed at home, either by the patient alone or with a care-giver. PD differs from Hemodialysis (HD) in that blood is not removed from the body and passed through a dialyzer, but rather a catheter is placed in the peritoneal cavity and dialysate introduced directly into the peritoneal cavity. Blood is cleaned inside the patient using the patient's own peritoneum as a type of dialysis membrane. However, because fluid is directly introduced into a human body, the fluid used for peritoneal dialysate is generally required to be free of biological and chemical contaminants. The peritoneal dialysate should also contain specified concentrations of solutes, buffer, osmotic agent and cations for biocompatibility and for performing membrane exchange.

Peritonitis is a serious and common problem in the PD population that results in abdominal pain, fever, and cloudy dialysate. Peritonitis remains a leading complication of PD with around 18% of infection-related mortality in PD patients resulting from peritonitis (Fried et al., "Peritonitis influences mortality in peritoneal dialysis patients," J. Am. Soc. Nephrol. 1996; 7:2176-2182). Moreover, peritonitis is a contributing factor to death in 16% of deaths on PD, and remains a major cause for patients discontinuing PD and switching to HD. Peritonitis and other peritoneal dialysis complications can oftentimes be traced to non-sterile techniques and/or contaminated starting dialysate.

The US FDA regulates pre-packaged dialysate for use in PD as a Class II drug if the pre-packaged dialysate is used in either an automatic or semi-automated PD system (e.g., cycler system). See 21 C.F.R. Sec. 876.5630. If the peritoneal dialysate is not pre-packaged, the US FDA requires the dialysate be prepared from a dialysate concentrate and "sterile purified water," which is defined by the FDA in 21 C.F.R. Sec. 165.110(a)(2)(iv) and (vii). Some possible contaminants present in water used to prepare dialysis fluid can be (i) particles, (ii) chemicals, and (iii) microbial contaminants such as bacteria, fungi and yeasts, and microbial derivatives or fragments (e.g., endotoxins released during active growth and lysis of micro-organisms). In additional to meeting purity and sterility requirements, peritoneal dialysate must also contain specific and precise amounts of solutes, such as sodium chloride, sodium bicarbonate, and cation infusates.

Because traditional peritoneal dialysis systems require FDA-approved, pre-packaged dialysate, the dialysate can be expensive due to high manufacturing, shipping, and storage costs. Shortages can also occur. These problems are not mitigated by on-site dialysate preparation because the source water must still meet high fluid purity and sterility characteristics. Such standards may be difficult to meet, particularly for continuous, automatic peritoneal dialysis machines designed for home use. Further, traditional systems usually require storage of hundreds of liters of dialysate bags, including 300 L or more of peritoneal dialysate and over 300 kg of fluid per month.

Known systems and methods require significant space to store peritoneal dialysate prior to use. Continuous ambulatory peritoneal dialysis (CAPD) traditionally uses 1-4 exchanges of peritoneal dialysate a day, with an overnight dwell. Because each exchange requires approximately 2-4 L of peritoneal dialysate, use of prepackaged dialysate requires storing about 8-16 L of dialysate per day, or 56-112 L of dialysate per week. Automated peritoneal dialysis uses a cycler to cycle peritoneal dialysis into and out of the peritoneal cavity of the patient, generally at night. APD generally uses 3-5 exchanges daily, requiring up to 20 L of dialysate per day and up to 140 L of dialysate per week. Tidal Peritoneal Dialysis (TPD) is similar to APD with the exception that a between 250 mL to 1000 mL of the peritoneal dialysate is left in the peritoneal cavity of the patient between infusions. The known systems and methods require significant storage space and can deter the adoption of CAPD, APD, or TPD.

There is a need for systems and methods that can generate peritoneal dialysate using water of varying quality. The need includes generating peritoneal dialysate on-demand, so that no extra space is required for storing peritoneal dialysate. Generating the peritoneal dialysate can be any one or more of automatic, selective, or continuous. The need includes peritoneal dialysate having purity and sterility requirements such that patients will not contract an infection due to bacteria or other pathogens in fluid used for peritoneal dialysate. The need is acute for automated fluid generation for continuous dialysis machines for use at home where a water source can be tap water or other non-sterile source. There is also a need for systems and methods that allow for automatically generating dialysate suitable for peritoneal dialysis containing proper amounts of solutes and cations.

There is further a need for a system that uses filtration, as opposed to heat, in sterilization of the dialysate, which reduces the generation of glucose degradation products. There is also a need for a system that can generate peritoneal dialysate on demand, or for direct infusion into the patient, reducing the storage time and space requirements, as well as lowering the probability of loss of sterility of the dialysate.

SUMMARY OF THE INVENTION

The first aspect of the invention relates to a peritoneal dialysis system. In any embodiment of the first aspect of the invention, the system has a water source; a peritoneal dialysate generation flow path; wherein the peritoneal dialysate generation flow path is fluidly connectable to the water source; one or more water purification modules fluidly connectable to the peritoneal dialysate generation flow path; a concentrate source fluidly connectable to the peritoneal dialysate generation flow path; the concentrate source containing one or more solutes; and a sterilization module fluidly connectable to the peritoneal dialysate generation flow path.

In any embodiment of the first aspect of the invention, the system has one or more dialysate containers fluidly connectable to the peritoneal dialysate generation flow path downstream of the sterilization module.

In any embodiment of the first aspect of the invention, the concentrate source includes one or more of an osmotic agent and an ion concentrate.

In any embodiment of the first aspect of the invention, the concentrate source includes at least an osmotic agent source and an ion concentrate source.

In any embodiment of the first aspect of the invention, the concentrate source includes multiple osmotic agent sources.

In any embodiment of the first aspect of the invention, the osmotic agent sources contain osmotic agents selected from the group of dextrose, icodextrin, amino acids and glucose.

In any embodiment of the first aspect of the invention, the ion concentrate source includes one or more from the group of sodium chloride, sodium lactate, magnesium chloride, calcium chloride, potassium chloride, and sodium bicarbonate.

In any embodiment of the first aspect of the invention, the concentrate source includes multiple ion concentrate sources.

In any embodiment of the first aspect of the invention, the system includes a concentrate pump positioned between the concentrate source and the peritoneal dialysate generation flow path for controlled addition of fluid from the concentrate source to the peritoneal dialysate generation flow path.

In any embodiment of the first aspect of the invention, the system includes multiple dialysate containers fluidly connectable to the peritoneal dialysate generation flow path.

In any embodiment of the first aspect of the invention, a volume of the dialysate container is between any of 1 to 20 L, 1 to 2 L, 1 to 3 L, 2 to 6 L, 2 to 4 L, 6 to 10 L, 8 to 10 L, 8 to 12 L, 10 to 12 L, 10 to 15 L, or 12 to 20 L.

In any embodiment of the first aspect of the invention, each dialysate container has a volume between any of 1 to 6 L, 1 to 3 L, 1.5 to 3 L, 2 and 4 L, or 3 to 6 L.

In any embodiment of the first aspect of the invention, the system includes one or more valves and one or more flow meters to control addition of peritoneal dialysate to each of the dialysate containers.

In any embodiment of the first aspect of the invention, the system includes a control system, wherein the control system operates one or more pumps and valves to control movement of fluid through the system.

In any embodiment of the first aspect of the invention, the control system has a timer, and wherein the timer causes the control system to generate peritoneal dialysate at a predetermined time.

In any embodiment of the first aspect of the invention, the control system has a user interface, wherein the user interface causes the control system to generate peritoneal dialysate at a selected time.

In any embodiment of the first aspect of the invention, the sterilization module can include one or more ultrafilters; a UV light source; a heater, a flash pasteurization module, a microbial filter; or combinations thereof.

In any embodiment of the first aspect of the invention, the sterilization module can include a UV light source positioned downstream of the ultrafilter.

In any embodiment of the first aspect of the invention, the sterilization module can include at least two ultrafilters.

In any embodiment of the first aspect of the invention, the water purification module includes one or more selected from the group of a sorbent cartridge, activated carbon, a reverse osmosis module, a carbon filter, and a nanofilter.

The features disclosed as being part of the first aspect of the invention can be in the first aspect of the invention, either alone or in combination, or follow a preferred arrangement of one or more of the described elements.

The second aspect of the invention is directed to a method. In any embodiment of the second aspect of the invention, the method includes the steps of pumping fluid from a water source to a water purification module in a peritoneal dialysate generation flow path; adding one or more concentrate solutions to the fluid; and pumping the fluid through a sterilization module.

In any embodiment of the second aspect of the invention, the method includes the step of pumping the fluid into one or more dialysate containers.

In any embodiment of the second aspect of the invention, the step of pumping the fluid into one or more dialysate containers includes pumping the fluid into multiple dialysate containers.

In any embodiment of the second aspect of the invention, wherein the step pumping the fluid into multiple dialysate containers includes pumping between any of 1 to 6 L, 1 to 3 L, 1.5 to 3 L, 2 to 4 L, or 3 L to 6 L into each dialysate container.

In any embodiment of the second aspect of the invention, the step of pumping the fluid into one or more dialysate containers includes pumping the fluid into a single dialysate container.

In any embodiment of the second aspect of the invention, the step pumping the fluid into a single dialysate container includes pumping between any of 1 to 6 L, 1 to 3 L, 1.5 to 3 L, 2 to 4 L, or 3 to 6 L into the single dialysate container.

In any embodiment of the second aspect of the invention, the step pumping the fluid into a single dialysate container includes pumping between any of 6 to 20 L, 6 to 10 L, 8 to 10 L, 8 to 12 L, 10 to 12 L, 10 to 15 L, or 12 to 20 L into the single dialysate container.

In any embodiment of the second aspect of the invention, the step of adding one or more concentrate solutions to the fluid includes adding at least an osmotic agent and an ion concentrate to the fluid.

In any embodiment of the second aspect of the invention, the osmotic agent and ion concentrate are added to the fluid from a single concentrate source.

In any embodiment of the second aspect of the invention, the osmotic agent and ion concentrate are added from separate concentrate sources.

In any embodiment of the second aspect of the invention, the osmotic agent is one or more selected from the group of glucose, dextrin, and icodextrin.

In any embodiment of the second aspect of the invention, the osmotic agent includes multiple osmotic agents.

In any embodiment of the second aspect of the invention, the multiple osmotic agents are added from a single source.

In any embodiment of the second aspect of the invention, each of the multiple osmotic agents are added from separate sources.

In any embodiment of the second aspect of the invention, the ion concentrate is added from one or more ion concentrate sources and includes one or more from the group of sodium chloride, sodium lactate, magnesium chloride, calcium chloride, potassium chloride, and sodium bicarbonate.

In any embodiment of the second aspect of the invention, each of the ion concentrates are added to the fluid from a single ion concentrate source.

In any embodiment of the second aspect of the invention, the ion concentrate source includes multiple ion concentrate sources; and wherein each of the multiple ion concentrate sources has different solutes.

In any embodiment of the second aspect of the invention, the step of adding one or more concentrate solutions to the fluid includes controlling an addition of concentrate from each of the ion concentrate sources to generate a fluid with a prescribed solute concentration.

In any embodiment of the second aspect of the invention, the method is carried out by a peritoneal dialysate generation system.

In any embodiment of the second aspect of the invention, the peritoneal dialysate generation system includes a timer; wherein the peritoneal dialysate generation system carries out the method at predetermined times.

In any embodiment of the second aspect of the invention, the peritoneal dialysate generation system includes a user interface, and the method is carried out based on input from the user interface.

In any embodiment of the second aspect of the invention, the water purification module includes one or more selected from the group of a sorbent cartridge, activated carbon, a reverse osmosis module, a carbon filter, and a nanofilter.

In any embodiment of the second aspect of the invention, the sterilization module can include one or more ultrafilters; a UV light source; a microbial filter; or combinations thereof.

In any embodiment of the first aspect of the invention, the sterilization module can include a UV light source positioned downstream of the ultrafilter.

In any embodiment of the first aspect of the invention, the sterilization module can include at least two ultrafilters.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
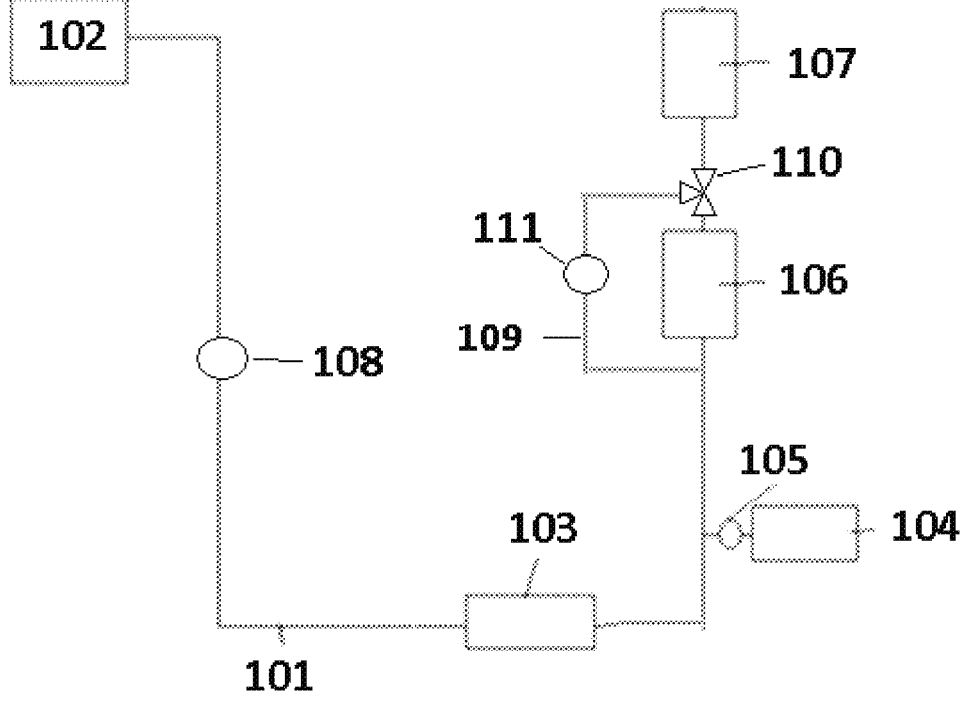
FIG. 1 shows a flow path for generating peritoneal dialysate.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

"Activated carbon" refers to a form of carbon processed to have small pores, increasing the surface area available for adsorption.

The term "amino acid," as used herein, refers to any nitrogen containing organic acid or peptide that can be used as an osmotic agent to generate peritoneal dialysate.

The term "calcium chloride source" refers to a source of calcium chloride in solid and/or solution form. The calcium chloride source can contain at least one fluid pathway and include components such as conduits, valves, filters or fluid connection ports, any of which are fluidly connectable to each other or to a fluid flow path. The calcium chloride source can either be formed as a stand-alone enclosure or a compartment integrally formed with an apparatus for dialysis for containing the calcium chloride source.

A "carbon filter" is a bed of activated carbon.

The term "comprising" includes, but is not limited to, whatever follows the word "comprising." Use of the term indicates the listed elements are required or mandatory but that other elements are optional and may be present.

A "concentrate pump" is a pump configured to move fluid between a concentrate source and a flow path.

A "concentrate solution" is a solution of one or more solutes in water. The concentrate solution can have a solute concentration greater than that to be used in dialysis.

A "concentrate source" is a source of one or more solutes. The concentrate source can have one or more solutes that has a solute concentration greater than the solute concentration to be used for dialysis.

A "connector" and "for connection" describe the concept of forming a fluid connection between two components wherein fluid, gas, or mixture of both gas and fluid can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" refers to the ability of one component to direct the actions of a second component.

A "control system" can be a combination of components acting together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The terms "controlled addition," to "control addition," or "controlling addition" refer to the ability to add one or more substances or fluids to a flow path or container in an accurately controllable amount.

The phrase "controlling the movement of fluid" refers to directing fluid through a flow path, container, receptacle, or reservoir of any type.

The term "dextrose source" refers to a source of dextrose in solid and/or solution form. The dextrose source can interface with at least one other module found in systems for dialysis. The dextrose source can contain at least one fluid pathway and include components such as conduits, valves, filters or fluid connection ports, any of which are fluidly connectable to each other or to a fluid flow path. The dextrose source can either be formed as a stand-alone enclosure or a compartment integrally formed with an apparatus for dialysis for containing a dextrose source.

The term "dialysate" describes a fluid into or out of which solutes from a fluid to be dialyzed diffuse through a membrane. Dialysate can differ depending on the type of dialysis to be carried out. For example, dialysate for peritoneal dialysis may include different solutes or different concentrations of solutes than dialysate for hemodialysis.

A "dialysate container" is any container capable of storing or containing dialysate for dialysis. The container any be of any suitable, size, geometry, or configuration.

The term "dialysis caddy" refers to a container detachably removable from a dialysis system, the caddy configured to hold one or more other containers. In any embodiment, the caddy can include one or more connectors for fluid connection from the containers to the dialysis system.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "fitting feature" is any protrusion, indentation, groove, ridge, having any shape, size, or geometry that ensures that only a corresponding fitting feature complementary to the fitting feature can form a connection or fit to the corresponding fitting feature. The fitting feature can also include non-mechanical means for ensuring complementary connection such as magnets placed at particular locations, or visual or aural indicators such as color, lettering, or sound. The fitting feature can be affixed, integral, or labeled on a component or surface to ensure a corresponding feature on a desired component or surface can mate or connect to the component or surface having the fitting feature.

A "flash pasteurization module" is a component or set of components capable of heating a fluid to a high temperature and recirculating the fluid for sterilization.

A "flow meter" is a device capable of measuring an amount or rate of fluid moving past or through a particular location.

The term "fluid" can be any substance without a fixed shape that yields easily to external pressure such as a gas or a liquid. Specifically, the fluid can be water containing any solutes at any concentration. The fluid can also be dialysate of any type including fresh, partially used, or spent.

The terms "fluid connection," "fluidly connectable," or "fluidly connected" refer to the ability to pass fluid or gas from one point to another point. The two points can be within or between any one or more of compartments, modules, systems, and components, all of any type.

The terms "to generate peritoneal dialysate" or "peritoneal dialysate generation" refers to creating a peritoneal dialysate solution from constituent parts.

The term "glucose source" refers to a source of glucose in solid and/or solution form. The glucose source can interface with at least one other module found in systems for dialysis. The glucose source can contain at least one fluid pathway and include components such as conduits, valves, filters or fluid connection ports, any of which are fluidly connectable to each other or to a fluid flow path. The glucose source can either be formed as a stand-alone enclosure or a compartment integrally formed with an apparatus for dialysis for containing a glucose source.

A "heater" is a component capable of raising the temperature of a substance, container, or fluid.

An "ion concentrate" refers to one or more ionic compounds. The ion concentrate can have one or more ionic compounds in the ion concentrate. Further, the ion concentrate can have an ion concentration greater than an ion concentration to be used in dialysis.

An "ion concentrate source" refers to a source of one or more ionic compounds. The ion concentrate source can be in water or solid form. The ion concentrate source can further have one or more ionic compounds that are at a higher ion concentration greater than generally used in dialysis.

The term "level of sterility" refers to an estimated probability of viable organisms surviving a sterilization process.

The term "magnesium chloride source" refers to a source of magnesium chloride in solid and/or solution form. The magnesium chloride source can interface with at least one other module found in systems for dialysis. The magnesium chloride source can contain at least one fluid pathway and include components such as conduits, valves, filters or fluid connection ports, any of which are fluidly connectable to each other or to a fluid flow path. The magnesium chloride source can either be formed as a stand-alone enclosure or a compartment integrally formed with an apparatus for dialysis for containing a magnesium chloride source.

The term "microbial filter" refers to a device inhibiting passage of microbes or fragments of microbes such as endotoxins in a fluid or solution while allowing the passage of the fluid or solution.

A "nanofilter" is a filter membrane having nanometer sized pores.

An "osmotic agent" is a substance dissolved in water capable of driving a net movement of water by osmosis across a semi-permeable membrane due to concentration differences of the osmotic agent on each side of the semi-permeable membrane.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters or fluid connection ports, any of which are fluidly connectable to each other or to a fluid flow path. The osmotic agent source can either be formed as a stand-alone enclosure or a compartment integrally formed with an apparatus for dialysis for containing an osmotic agent source.

"Peritoneal dialysate" is a dialysis solution to be used in peritoneal dialysis having specified parameters for purity and sterility. Peritoneal dialysate is not the same as dialysate used in hemodialysis although peritoneal dialysate may be used in hemodialysis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. This cycle can be repeated for several cycles each day or as needed.

A "peritoneal dialysate generation flow path" is a path used in generating dialysate suitable for peritoneal dialysis.

The term "prescribed solute concentration" refers to the concentration of one or more solutes in peritoneal dialysate intended for use by a patient.

A "predetermined time" is a set time for an event to occur, such as a set time of day, or a set length of time from a previous event.

The term "pump" refers to any device which causes the movement of fluids or gases by applying suction or pressure.

The terms "pumping fluid" or to "pump fluid" refer to moving a fluid through a flow path with a pump.

A "purified water source" is a water source containing purified water.

"Purified water" can be defined as water produced by distillation, deionization, reverse osmosis, or other suitable processes and meets the definition of "purified water" in the United States Pharmacopeia, 23d Revision, Jan. 1, 1995, and the FDA at 21 CFR Section § 165.110(a)(2)(iv). Other criteria for purified water can be determined by those of skill in the art, particularly as relating to purified water suitable for peritoneal dialysis.

A "reverse osmosis module" is a set of components to drive fluid through one or more semipermeable membranes, wherein pressure is used to move the fluid from a side of the semipermeable membrane with a higher concentration of one or more solutes to a side of the semipermeable membrane with a lower concentration of the one or more solutes.

The term "sodium chloride source" refers to a source of sodium chloride in solid and/or solution form. The sodium chloride source can interface with at least one other module found in systems for dialysis. The sodium chloride source can contain at least one fluid pathway and include components such as conduits, valves, filters or fluid connection ports, any of which are fluidly connectable to each other or to a fluid flow path. The sodium chloride source can either be formed as a stand-alone enclosure or a compartment integrally formed with an apparatus for dialysis for containing a sodium chloride source.

The term "sodium lactate source" refers to a source of sodium lactate in solid and/or solution form. The sodium lactate source can interface with at least one other module found in systems for dialysis. The sodium lactate source can contain at least one fluid pathway and include components such as conduits, valves, filters or fluid connection ports, any of which are fluidly connectable to each other or to a fluid flow path. The sodium lactate source can either be formed as a stand-alone enclosure or a compartment integrally formed with an apparatus for dialysis for containing a sodium lactate source.

A "solute" is a substance dissolved in a solvent, such as water.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents capable of removing solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

A "sterilization module" is a component or set of components to sterilize a fluid by removing or destroying chemical or biological contaminants.

A "timer" is a device capable of determining the time of day, or the time elapsed between multiple events.

An "ultrafilter" is a semi permeable membrane through which a fluid can pass with removal of one or more solutes or particles from the fluid.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "user interface" is a component that allows a user to communicate information or instructions to a processor or a memory device and to receive information or instructions from the processor or memory device.

A "UV light source" is a component which uses ultraviolet light to kill biological contaminants in a fluid.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

The term "water purification module" refers to a component or components capable of removing biological or chemical contaminants from water.

The term "water source" refers to a source from which potable water can be obtained.

"Zirconium oxide" refers to a polymer of the form $ZrO_2$ with one or more anionic molecules adsorbed onto the surface of the zirconium oxide polymer. In any embodiment, the zirconium oxide polymer can act as an anion exchange material, removing anions from a fluid for the anions originally adsorbed onto the surface of the zirconium oxide.

"Zirconium phosphate" refers to a material of the form $Zr(HPO_4)_2$, with or without water molecules associated as hydrates. The zirconium phosphate material can have one or more cationic species adsorbed into the material, which can be exchanged with cations present in a fluid to which the zirconium phosphate is exposed.

Peritoneal Dialysis System

The first and second aspects of the invention relate to systems and methods for generating a peritoneal dialysate solution. The solution can be generated continuously or in a bolus. The peritoneal dialysate can be generated in advance of peritoneal dialysis and stored for later use with a non-integrated cycler. In any embodiment of the first or second aspects of the invention, a system for generating peritoneal dialysate can be configured as illustrated in FIG. 1. The system includes a peritoneal dialysate generation flow path 101. Fluid from a water source 102 can be pumped into the peritoneal dialysate generation flow path 101. System pump 108 can control the movement of fluid through the peritoneal dialysate generation flow path 101. The system pumps the fluid from water source 102 through a water purification module 103 to remove chemical contaminants in the fluid in preparation for creating peritoneal dialysate.

In any embodiment of the first or second aspects of the invention, the water source 102 can be a source of potable water including a purified water source. Purified water can refer to water meeting the definition of "purified water" in the United States Pharmacopeia, 23d Revision, Jan. 1, 1995. Alternatively, purified water can refer to any source of water treated to remove at least some biological or chemical contaminants, whether or not the water meets the definition of purified water in United States Pharmacopeia, 23d Revision, Jan. 1, 1995. In any embodiment of the first or second aspects of the invention, the water source 102 can be a non-purified water source, such as tap water, wherein the water from the water source 102 can be purified by the system as described. The system can be directly connected to a tap or faucet to provide non-purified water that can be purified by the system. A non-purified water source can provide water without additional purification, such as tap water from a municipal water source, water that has undergone some level of purification, but does not meet the definition of "purified water" provided, such as bottled water or filtered water. In any embodiment, the water source can contain water meeting the WHO drinkable water standards provided in *Guidelines for Drinking Water Quality*, World Health Organization, Geneva, Switzerland, 4th edition, 2011. The peritoneal dialysate generation flow path 101 can also be connected to a purified or non-purified water source such as a tap or faucet line. The water source can be any source of water, whether from a tap, faucet, or a separate container or reservoir. The water source 102 can be any size usable with the system, including between 12 and 20 L. A water source 102 of 15 L can generally generate the necessary peritoneal dialysate for multiple cycles.

In any embodiment of the first or second aspects of the invention, the water purification module 103 can be a sorbent cartridge. The sorbent cartridge includes an anion exchange material such as zirconium oxide. The zirconium oxide can remove anionic species from the fluid, such as phosphate or fluoride molecules, replacing the anionic species with acetate or hydroxide ions. The sorbent cartridge can have any anion exchange material known in the art capable of removing anionic species from the fluid. In any embodiment, the sorbent cartridge can include aluminum oxide for removal of fluoride and heavy metals. Alternatively, the water purification module 103 can be a combination of ion and anion exchange materials. The sorbent cartridge can be sized depending on the needs of the user, with a larger sized sorbent cartridge allowing for more exchanges before the sorbent cartridge must be replaced.

The sorbent cartridge can include a cation exchange material, such as zirconium phosphate. The zirconium phosphate can remove cationic species from the fluid, such as potassium, calcium, magnesium, or other cations, replacing the cationic species with hydrogen or sodium. The sorbent cartridge can include any cation exchange material capable of removing cations from the fluid.

The sorbent cartridge can also include activated carbon. The activated carbon operates to adsorb non-ionic molecules, organic molecules, and chlorine from the water, along with some endotoxins or bacterial contaminants. The activated carbon can be present in the sorbent cartridge in the form of a carbon filter or pad, or as a material layer in the sorbent cartridge. A carbon filter or pad is a bed of activated carbon. The carbon filter can be in a self-contained packaging, or present as a layer of activated carbon within the sorbent cartridge. The sorbent cartridge can purify up to 3 L of water per exchange for a single infusion, with flow rates of up to 300 ml/min. A larger sorbent cartridge can be used when generating peritoneal dialysate for multiple infusions, including a sorbent cartridge that can purify between 3 and 20 L, between 3 and 5 L, between 3 and 10 L, between 5 and 12 L, between 10 and 15 L, or between 10 and 20 L of water, or more.

In any embodiment, the sorbent cartridge can be a single use component or a rechargeable component. Recharging can refer to the process of treating a sorbent material to restore the functional capacity of the sorbent material so as to put the sorbent material back into a condition for use or reuse in a new dialysis session. In some instances, recharging also includes treating a sorbent material so as to clean the sorbent material so that the sorbent material can be stored and used in a subsequent dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

The sorbent cartridge can additionally include a microbial filter and/or a particulate filter. A microbial filter can further reduce the amount of endotoxins or bacterial contaminants present in the fluid from the water source 102. A particulate filter can remove particulate matter from the fluid.

Alternatively, the water purification module 103 can be any component capable of removing contaminants from the water in the water source 102, including any one or more of a sorbent cartridge, reverse osmosis module, nanofilter, combination of ion and anion exchange materials, activated carbon, silica, or silica based columns.

Upon passing through water purification module 103, fluid can be pumped to a concentrate source 104 where necessary components for carrying out peritoneal dialysis can be added from the concentrate source 104. The concentrates in the concentrate source 104 are utilized to create a peritoneal dialysis fluid that matches a dialysis prescription. Concentrate pump 105 can control the movement of concentrates from the concentrate source 104 to the peritoneal dialysate generation flow path 101 in a controlled addition. The concentrates added from the concentrate source 104 to the peritoneal dialysate generation flow path 101 can include any component prescribed for use in peritoneal dialysate. Table 1 provides non-limiting exemplary ranges of commonly used components of peritoneal dialysate.

TABLE 1

| Component | Concentration |
| --- | --- |
| Sodium chloride | 132-134 mmol/L |
| Calcium chloride dehydrate | 1.25-1.75 mmol/L |
| Magnesium chloride hexahydrate | 0.25-0.75 mmol/L |
| Sodium Lactate | 35-40 mmol/L |
| Dextrose (D-glucose) monohydrate | 0.55-4.25 g/dL |
| pH | 5-6 |
| Osmolality | 346-485 (hypertonic) |

To reduce the glucose degradation products (GDP) formed by heating conventional peritoneal dialysate, some peritoneal dialysate systems use a low GDP formulation. Exemplary peritoneal dialysate concentrations for low GDP formulations are provided in Table 2. Generally, the low GDP peritoneal dialysate is provided in two separate bags, with one bag containing calcium chloride, magnesium chloride and glucose maintained at low pH, and the second bag containing sodium chloride and the buffer components, including sodium lactate and sodium bicarbonate. The two bags are mixed prior to use to generate a peritoneal dialysate with a neutral pH. Alternatively, a two chamber bag is used, the chambers separated by a divider which is broken to mix the fluids prior to use.

TABLE 2

Low GDP peritoneal dialysate formulations

| Component | Concentration |
| --- | --- |
| Sodium | 132-134 mEq/L |
| Calcium | 2.5-3.5 mEq/L |
| Magnesium | 0.5-1.0 mEq/L |
| Lactate | 0-40 mEq/L |
| Bicarbonate | 0-34 mEq/L |
| pH | 6.3-7.4 |
| % glucose (g/dL) | 1.5-4.25 |

One of skill in the art will understand other components can be used in place of the components listed in Tables 1-2. For example, dextrose as listed in Table 1 is commonly used as an osmotic agent. In any embodiment of the first or second aspects of the invention, other osmotic agents can be used in addition to, or in place of, the dextrose, including glucose, icodextrin or amino acids, including dialysate with multiple osmotic agents. Although the sources of sodium, calcium, and magnesium listed in Table 1 are chloride salts, other sodium, magnesium, and calcium salts can be used, such as lactate or acetate salts. Peritoneal dialysate may also contain buffers for maintaining pH of the peritoneal dialysate. Exemplary, non-limiting examples of suitable buffers include bicarbonate buffer, acetate buffer or lactate buffer. Although not generally used in peritoneal dialysis, potassium chloride can be used for hypokalemic patients who don't receive sufficient potassium through diet. The concentrate source 104 can contain one or more osmotic agents, as well as one or more ion concentrates, such as concentrated sodium chloride, sodium lactate, magnesium chloride, calcium chloride, and/or sodium bicarbonate. The concentrate source 104 can be a single source of concentrates, including both osmotic agents and ion concentrates, or can include multiple sources of concentrates, with separate sources for the osmotic agents and ion concentrates. In any embodiment, the system can have a single concentrate that has all components mixed for a daytime or overnight treatment for use in a home by a single patient. Alternatively, the concentrate source 104 can include separate sources for any one or more of the solutes to be used in the peritoneal dialysate each with a separate concentrate pump to add each component needed to create the peritoneal dialysate. Concentrate pump 105 pumps concentrated solutions from the concentrate source or sources 104 to the peritoneal dialysate generation flow path 101 in a controlled addition. Where more than one concentrate source is used, separate concentrate pumps can move each of the concentrates into the peritoneal dialysate generation flow path 101, or a single concentrate pump can be used, with valves configured allow individual control over the movement of each of the concentrate solutions to the peritoneal dialysate generation flow path 101.

After addition of solutes from the concentrate source 104, the fluid in the peritoneal dialysate generation flow path 101 can contain all the necessary solutes for peritoneal dialysis. The peritoneal dialysate should reach a level of sterility suitable for peritoneal dialysis. The level of sterility can be any level meeting an applicable regulatory requirement, such as a sterility assurance level of $10^{-6}$ required by the FDA, meaning the chance of a viable organism present after sterilization is 1 in 1,000,000. The system can pump the fluid to a sterilization module 106 for sterilization of the peritoneal dialysate. A sterilization module recirculation line 109 can convey the fluid through the sterilization module 106 multiple times. Valve 110 and pump 111 can control the movement of fluid through the sterilization module recirculation line 109.

The sterilization module 106 can be any component or set of components capable of sterilizing the peritoneal dialysate. In any embodiment, the sterilization module can be one or more ultrafilters to provide redundancy of the system to protect against sterilization failure A secondary component, such as a UV light source or microbial filter, can be included in the sterilization module 106 to provide additional sterilization of the peritoneal dialysate. The UV light source can be positioned at any location in the peritoneal dialysate generation flow path 101, including between the first and second ultrafilters, upstream of the one or more ultrafilters, or downstream of the one or more ultrafilters. The sterilization module can also include a microbial filter. The ultrafilters used in the sterilization module can be replaced as necessary. In any embodiment, the ultrafilters can have a 3-6-month lifetime before replacement. The ultrafilters can be any ultrafilter known in the art capable of sterilizing the peritoneal dialysate. A non-limiting example of an ultrafilter that can be used in the systems described is the hollow fiber ForClean ultrafilter, available from Bellco, Mirandola (MO), Italy. In certain embodiments, the sterilization module 106 can use heat sterilization. The sterilization module 106 can include a heater to heat the prepared dialysate. Alternatively or additionally, the sterilization module 106 can include a flash pasteurization module to sterilize the dialysate through flash pasteurization. The sterilization module 106 can include both heat-based sterilization components and filtration based sterilization components, with the user adjusting the mode of sterilization based on the mode of use. For example, a heat based sterilization can be used when the peritoneal dialysate is generated for later use, while a filtration based sterilization can be used when the peritoneal dialysate is generated for immediate use.

After sterilization of the fluid by the sterilization module 106, the generated peritoneal dialysate can be pumped to a dialysate container 107 for storage until ready for use by a patient. The dialysate container 107 can include one or more sterilized dialysate bags. The dialysate bags, once filled with peritoneal dialysate, can be stored until needed by the patient. The filled dialysate container 107 can be removed from the system and connected to a catheter or a non-integrated cycler for infusion of the peritoneal dialysate into a patient. The dialysate container can alternatively be a reusable sterilized container or bag. The reusable container or bag can be cleaned and sterilized daily, or at set time periods. Alternatively, the dialysate container 107 can be any type of storage container, such as a stainless steel container. The connectors to the dialysate container 107 can be any type of connector known in the art.

The dialysate container 107 can store peritoneal dialysate sufficient for a single infusion of peritoneal dialysate into the patient. By generating peritoneal dialysate for a single infusion in real-time, and then immediately using the peritoneal dialysate, the dialysate storage time can be reduced, reducing the possibility of bacterial growth. A user interface can be included on the peritoneal dialysis generation machine, allowing a patient to direct the generation of peritoneal dialysate as needed. Additionally, or alternatively, the peritoneal dialysate machine can include a timer, and the timer can cause the peritoneal dialysate machine to generate peritoneal dialysate at predetermined times according to the patient's peritoneal dialysis schedule. Alternatively, the peritoneal dialysate generation machine can be equipped with wireless communication, such as Wi-Fi, BlueTooth, Ethernet, or any other wireless communication system known in the art. The user can direct the peritoneal dialysis machine to generate peritoneal dialysate at a specified time from any location. By using a timer, user interface, or wireless communication to control the generation of peritoneal dialysate, the peritoneal dialysate storage time can be reduced, lowering the chances of generating significant amounts of degradation products or allowing bacterial growth. In the case of power failure, an optional battery back-up can be included in the system.

In any embodiment of the first or second aspects of the invention, the dialysate container 107 can store enough peritoneal dialysate for multiple infusions into the patient, including enough peritoneal dialysate for one day or more of treatment. A timer can cause the machine to generate fresh peritoneal dialysate each day or at set times.

The dialysate container 107 can include multiple dialysate containers, each large enough to store enough peritoneal dialysate for a single infusion into the patient including between any of 1 to 6 L, 1 to 3 L, 1.5 to 3 L, 2 to 4 L, or 3 L to 6 L of dialysate. Alternatively, each of the one or more dialysate containers 107 can store enough peritoneal dialysate for multiple infusions into a patient, such as an entire day's amount of peritoneal dialysate including between any of 1 to 20 L, 1 to 2 L, 1 to 3 L, 2 to 6 L, 2 to 4 L, 6 to 10 L, 8 to 10 L, 8 to 12 L, 10 to 12 L, 10 to 15 L, or 12 to 20 L of peritoneal dialysate. If the dialysate containers 107 store peritoneal dialysate for multiple infusions into the patient, the same container can be used for each infusion with any suitable peritoneal dialysate cycler known in the art that can be fluidly connected to and used with the described system. Additional or alternative storage containers can be included at other locations in the peritoneal dialysate generation flow path 101. A storage container can be included upstream of the sterilization module, and downstream of the water purification module. Before the fluid is utilized in the cycler stage, the fluid can be pumped through the sterilization module, eliminating issues related to storage of sterile fluid. The storage containers can be either upstream or downstream of the concentrate source 104. The addition of concentrates to the fluid can happen either before storage of the fluid, or after storage of the fluid just before sterilization in the sterilization module.

As illustrated in FIG. 1, the necessary solutes can be added to the peritoneal dialysate generation flow path 101 from a single concentrate source 104. The solutes can be present in concentrated from within the concentrate source 104 in a fixed ratio for peritoneal dialysis, as shown in Table 1. Using a single concentrate source 104 for all solutes results in peritoneal dialysate having a fixed ratio of each of the solutes.

Table 3 provides exemplary non-limiting ranges of solutes for addition from a single concentrate source to the peritoneal dialysate generation flow loop, including the starting concentration of the solutes in the concentrate source, as well as exemplary final volumes of the solutes in the dialysate and the exemplary flow rates of both the solutes and the water in the dialysate generation flow loop to achieve the listed concentrations. The solutes shown in Table 3 are traditional peritoneal dialysate solutes. Table 4 shows exemplary ranges of solutes for a low GDP formulation. Table 5 shows exemplary ranges of solutes with icodextrin as the osmotic agent. Icodextrin is sometimes used as an osmotic agent for a long dwell period. If dextrose or glucose is used in a long dwell period, reabsorption of the ultrafiltrate can occur, reducing the net volume of fluid removed. Icodextrin results in a long sustained ultrafiltration, and can provide improved ultrafiltration efficiency over a long dwell period. One of skill in the art will understand the concentrations of any of the solutes shown in Tables 3-5 can be altered by altering the flow rates of the system pump or concentrate pump. However, the ratio of the solutes included is fixed when using a single concentrate source. If the ratio of the solutes needs to be altered for any reason, a new concentrate solution may be needed.

TABLE 3

| Exemplary solutes for addition from a single concentrate source | | | |
| --- | --- | --- | --- |
| Component | Concentration (g/l) | Solution volume (ml/L) | Flow rate (ml/min) |
| Glucose | 100-850 | 50-400 | 1-18 |
| Sodium Chloride | 13-108 | 50-400 | 1-18 |
| Sodium Lactate | 11-90 | 50-400 | 1-18 |
| $MgCl_2 \cdot 6H_2O$ | 0.13-1.02 | 50-400 | 1-18 |
| $CaCl_2 \cdot 2H_2O$ | 0.6-5.1 | 50-400 | 1-18 |
| Water | | 600-950 | 50-1000 |

TABLE 4

| Exemplary solute ranges in a low GDP solution | | | |
| --- | --- | --- | --- |
| Component | Concentration (g/l) | Solution volume (ml/L) | Flow rate (ml/min) |
| Glucose | 100-900 | 50-400 | 1-18 |
| Sodium Chloride | 13-108 | 50-400 | 1-18 |
| Sodium Lactate | 11-90 | 50-400 | 1-18 |
| $MgCl_2 \cdot 6H_2O$ | 0.13-1.02 | 50-400 | 1-18 |
| $CaCl_2 \cdot 2H_2O$ | 0.6-5.1 | 50-400 | 1-18 |
| Water | | 600-950 | 50-1000 |

TABLE 5

| Exemplary solute ranges in icodextrin solution | | | |
|---|---|---|---|
| Component | Concentration (g/l) | Solution volume (ml/L) | Flow rate (ml/min) |
| Icodextrin | 100-850 | 100-400 | 2-37 |
| Sodium Chloride | 13-108 | 100-400 | 1-18 |
| Sodium Lactate | 11-90 | 100-400 | 2-37 |
| $MgCl_2 \cdot 6H_2O$ | 0.13-1.02 | 100-400 | 2-37 |
| $CaCl_2 \cdot 2H_2O$ | 0.6-5.1 | 100-400 | 2-37 |
| Water | | 600-900 | 50-1000 |

Although using a single concentrate source in the system requires a fixed ratio of solutes in the generated peritoneal dialysate, a single concentrate source provides certain advantages. Storage requirements are decreased, as only a single concentrate solution needs to be stored for a given dialysate prescription. There is also a lower risk of patient error in adding solutes to the dialysate in the proper amounts. A single concentrate source also requires less supplies, less pumps, and less hardware. Further, because fewer containers are needed, the containers are easier to manage, clean, and disinfect. One of skill in the art will understand a higher concentration of solutes in the concentrate source will allow minimization of the container size and maximization of the source water used in PD solution preparation, lowering costs. The limiting factor is mutual solubility of the components, which is generally limited by glucose or icodextrin solubility. The flow rate for the source water can be optimized to adjust the time required to prepare the solution. In the case of on-demand dialysate preparation, a high flow rate is desired to minimize the time needed to prepare the solution. The flow rate limit will be controlled by the metering accuracy of the concentrate pump at the rate required to match the water feed. With a single concentrate source, about 150 ml/exchange can be needed, corresponding to about 600 ml/day or 4.2 L/week. The concentrate source can be sized depending on the needs of the user, with a larger concentrate source requiring less frequent refilling.

The system can also include a waste container (not shown in FIG. 1) to collect any generated waste fluid as well as used peritoneal dialysate. The waste container collects effluent generated during disinfection and/or effluent generated by the purification modules, such as a reverse osmosis system. Alternatively, the waste fluid and used peritoneal dialysate can be directed to a drain for disposal.

In any embodiment of the first or second aspects of the invention, the peritoneal dialysate generation flow path 101 can be disinfected with a disinfection solution through on-board disinfection. The peritoneal dialysate generation flow path 101 can be configured to form a loop by connecting the portion of the peritoneal dialysate generation flow path 101 connecting to water source 102 to the portion of the peritoneal dialysate generation flow path 101 connecting to dialysate container 107. The disinfection solution can be introduced into the peritoneal dialysate generation flow path 101 and recirculated through the fluid lines by system pump 108. The disinfection solution can be a peracetic acid solution, a citric acid solution, a bleach solution, or any other suitable disinfection solution known in the art. The disinfectant can be heated by a heater (not shown) to any temperature capable of disinfecting the system, including temperatures of 90° C. or greater. The disinfectant can be introduced to the flow loop and recirculated at elevated temperatures to ensure complete disinfection. The connectors and components of the system can be gamma and autoclave compatible to resist the high temperatures used during disinfection. The system can be primed by introducing a priming fluid to the peritoneal dialysate generation flow path 101.

The peritoneal dialysate generation flow path illustrated in FIG. 1 can be part of a modular peritoneal dialysate system. Once generated, the peritoneal dialysate can be used by any non-integrated cycler. The patient can remove the filled peritoneal dialysate container and attach the container to a non-integrated cycler of any type. Alternatively, a hemostatic connection to a non-integrated cycler or peritoneal dialysate fluid infusion catheter can be included for infusion of the peritoneal dialysate. If using a hemostatic connection to a non-integrated cycler or peritoneal dialysate fluid infusion catheter, any one of a heater and temperature sensor can also be included. The temperature sensor can be positioned in the flow path to monitor the peritoneal dialysate after being generated and heated. The modularity of the system allows the patient to generate peritoneal dialysate as needed and to use the peritoneal dialysate with any suitable cycler known in the art.

Figure 2:
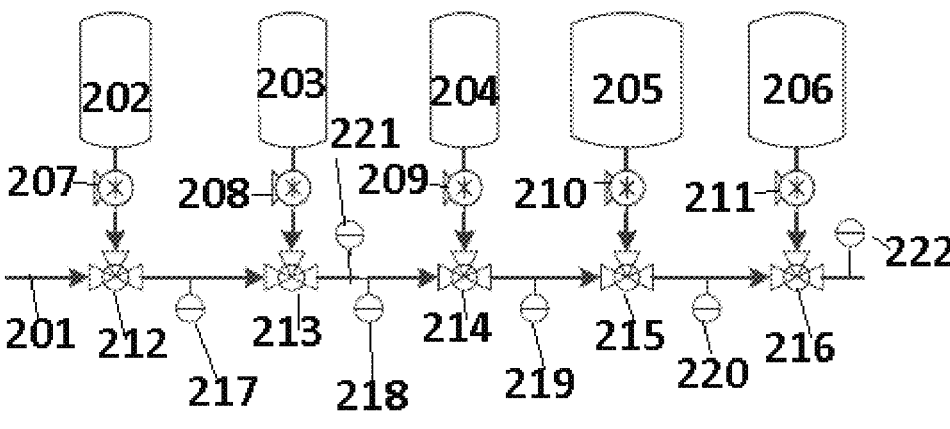
FIG. 2 shows a system for adding concentrates to a peritoneal dialysate generation flow path.

In any embodiment of the first or second aspects of the invention, solutes can be added to the peritoneal dialysate generation flow path from two or more separate concentrate sources, as shown in FIG. 2. The peritoneal dialysate generation flow path 201 can be fluidly connected to a water source and a water purification module upstream of the concentrate sources 202-206, and fluidly connected to a sterilization module and dialysate container downstream of the concentrate sources 202-206, as illustrated in FIG. 1.

As illustrated in FIG. 2, the concentrate source can include one or more ion concentrate sources, such as sodium chloride source 202 containing sodium chloride to be added in a controlled addition to the peritoneal dialysate generation flow path 201 by concentrate pump 207 through valve 212, sodium lactate source 203 containing sodium lactate to be added in a controlled addition to the peritoneal dialysate generation flow path 201 by concentrate pump 208 through valve 213, magnesium chloride source 204 containing magnesium chloride to be added in a controlled addition to the peritoneal dialysate generation flow path 201 by concentrate pump 209 through valve 214, and calcium chloride source 205 containing calcium chloride to be added in a controlled addition to the peritoneal dialysate generation flow path 201 by concentrate pump 210 through valve 215. One of skill in the art will understand other ions can be used in formulation of peritoneal dialysate, and each can be contained in a separate ion concentrate source or combined into one or more combined ion concentrate sources. The concentrate source also includes one or more osmotic agent sources, such as dextrose source 206 containing dextrose to be added to the peritoneal dialysate generation flow path 201 by concentrate pump 211 through valve 216. Any of the concentrate pumps can include flow meters to control the addition of the solutes. A glucose source and/or an icodextrin source can be used in addition to, or in place of, dextrose source 206. Multiple osmotic agents can be added to the peritoneal dialysate generation flow path 201 from one or more osmotic agent sources. One of skill in the art will understand other solutes can be used alternatively to, or in addition to, the solutes illustrated in FIG. 2. Any set of solutes used for peritoneal dialysate is within the scope of the invention. A control system in electronic communication with each of the concentrate pumps can control the movement of fluid from the concentrate sources to the peritoneal dialysate generation flow path 201. The amount of each of the concentrates moved into the peritoneal dialysate generation flow path 201 can be controlled to result in peritoneal dialysate having a prescribed solute concentration, as determined by a doctor or health care provider. The valves 212-216 can optionally be replaced with hose T junctions with additional components for preventing backflow into the concentrate source line if that particular line was not being used. A hose T is a fluid connector in a T-shape, with a port at each end for fluid to enter or exit the hose T. Optional sensors 217, 218, 219, and 220 ensure the solute concentration in the dialysate is at the correct level after each addition. The sensors 217-220 can be any type of sensor appropriate to confirm delivery of the concentrate, such as conductivity sensors. Optional pH sensor 221 ensures the pH is a proper level after addition of sodium lactate or other buffer. Optional refractive index meter 222 ensures the dextrose or other osmotic agent concentration in the dialysate is at the prescribed level. An additional sensor can be included upstream of sodium chloride source 202 for sensing the conductivity of the water prior to addition of concentrates. One of skill in the art will understand that additional sensor arrangements can be used in the described system. Any number of sensors can be included to monitor the peritoneal dialysate concentration, including 1, 2, 3, 4, 5, 6, 7, or more sensors. The concentrate sources can contain the solutes in either solid, powdered, or solution form. A solid or powdered source of solutes can be dissolved by the system by drawing fluid from the peritoneal dialysate generation flow path 201 into the concentrate source to generate a solution with a known concentration, such as a saturated solution of the solutes. The resulting solution is added to the peritoneal dialysate generation flow path as explained. Optionally, a heater (not shown) can periodically disinfect peritoneal dialysate generation flow path 201 at a temperature of at least 90° C. During periodic disinfection, the peritoneal dialysate generation flow path 201 can also be formed into a closed loop to circulate a disinfectant.

Although shown as a refractive index meter 222 in FIG. 2, one of skill in the art will understand alternative methods of measuring the osmotic agent concentration can be used. In any embodiment, enzyme-based sensors can detect the concentration of the osmotic agent in the dialysate. Enzyme based sensors use an enzyme capable of oxidizing the osmotic agent, such as glucose or dextrose. The enzyme is immobilized on an electrode and covered in a membrane through which the osmotic agent can pass. The electrode is used to electrochemically measure the change in either the oxidant, such as oxygen, or the product of glucose oxidation, such as hydrogen peroxide. Alternatively, electron transfer between the electrode and the enzyme can be detected with mediators, such as ferrocene to facilitate electron transfer. The osmotic agents can alternatively be detected through pulsed amperometric detection (PAD). PAD can detect glucose by applying a positive potential to a sample, resulting in oxidation of the glucose. The oxidation products are adsorbed onto the electrode and then desorbed by applying a more positive potential. Applying the more positive potential results in formation of an oxide layer on the electrode leading to passivation of the electrode surface. The catalytic activity of the electrode is then restored by application of a more negative potential, resulting in dissolution of the oxide layer.

Although illustrated as a single concentrate source in FIG. 1, and five separate concentrate sources in FIG. 2, one of skill in the art will understand that any number of concentrate sources can generate the peritoneal dialysate, including 1, 2, 3, 4, 5, 6, 7, or more concentrate sources. Any two or more of the separate concentrate sources illustrated in FIG.

2 can be combined into a single solute source, such as by combining all or some of the ion concentrate sources into a single ion concentrate source, where the mixed contents do not cause precipitation of the mixed concentrates.

Although each concentrate source is illustrated in FIG. 2 with a separate concentrate pump and fluid line, one of skill in the art will understand that more than one concentrate source can use a single pump and fluid line, with valves arranged thereon for controlled addition to the peritoneal dialysate generation flow path 201.

The concentrate sources 202-206 can be single use concentrate sources or disposable concentrate sources. The disposable concentrate sources are used in a single peritoneal dialysate generation process and then disposed. Multiple use concentrate sources are used repeatedly, and refilled as necessary with the solute.

Table 6 provides exemplary, non-limiting, ranges of for addition to the peritoneal dialysate using a separate osmotic agent source, glucose in Table 6, and a separate ion concentrate source containing sodium chloride, sodium lactate, magnesium chloride, calcium chloride and sodium bicarbonate. Because the glucose is added separately from the ion concentrates, the ratio of glucose to the other solutes can be varied depending on the needs of the patient.

TABLE 6

| Exemplary ranges of solutes in a two-concentrate source system | | | |
| --- | --- | --- | --- |
| Component | Concentration (g/l) | Solution volume (ml/L) | Dialysate composition |
| Part A | | | |
| Glucose | 850 | 6-53 | 0.55-4.5 g/dL |
| Part B | | | |
| NaCl | 269 | 20 | 92 mmol/L |
| Sodium Lactate | 84 | 20 | 15 mmol/L |
| $MgCl_2 \cdot 6H_2O$ | 5 | 20 | 0.5 mmol/L |
| $CaCl_2 \cdot 2H_2O$ | 18 | 20 | 2.5 mmol/L |
| $NaHCO_3$ | 105 | 20 | 25 mmol/L |
| Water | | 927-979 | 56.10 |

By using multiple concentrate sources, greater individualization and therapy customization can be achieved for each patient. With a single concentrate source, all solutes in the generated peritoneal dialysate must be present in a fixed ratio. By using more than one concentrate source, the ratio of solutes used in the peritoneal dialysate can be altered as the concentration of each of the osmotic agent and ion solutes can be individually controlled. For example, as illustrated by Table 6, with a single ion concentrate source and a single osmotic agent source, peritoneal dialysate with greater or less osmotic agent per concentration of ions can be generated, providing the ability to adjust the tonicity of the peritoneal dialysate solution independently of the electrolyte composition to meet the UF needs of any patient with a single set of solutions and allowing greater control over ultrafiltration. The ultrafiltration rate resulting from using the peritoneal dialysate solutions can be altered by altering the concentration of the osmotic agent independently of the ionic solutes, or by changing the osmotic agent used. For example, typical ultrafiltration volumes using dextrose as the osmotic agent vary with the dextrose concentration of the peritoneal dialysate. With a 1.5% dextrose solution, the typical ultrafiltration volume is about 150 mL. With a 2.5% dextrose solution, the typical ultrafiltration volume is about 250 mL. With a 4.25% dextrose solution, the typical ultrafiltration volume can exceed 600 mL. For a single exchange using separate concentrate sources for the ion concentrates and the osmotic agent, about 50 mL of the ion concentrate and 150 mL of the osmotic agent may be needed, corresponding to about 200 ml/day or 1.4 L/week of the ion concentrate and 600 ml/day or 4.2 L/week of the osmotic agent.

Because the system is not limited to discrete glucose or other osmotic agent concentrations like known commercial solutions; the system can customize the peritoneal dialysate solutions to meet the ultrafiltration needs of patient as determined by a healthcare provider. As illustrated in Table 6, the glucose level in the peritoneal dialysate solution can be varied from 0.55 g/dL to 4.5 g/dL, while maintaining the electrolytes and buffer components constant. Varying the glucose level while maintaining the electrolyte and buffer components constant allows the system to cover the range of glucose formulations currently offered commercially using a single Part A and Part B composition.

In any embodiment of the first or second aspects of the invention, two osmotic agent sources can be used, such as a dextrose source and an icodextrin source. With two osmotic agent sources one could use dextrose during the daytime exchanges for CAPD and icodextrin during the night dwell to take advantage of the higher UF removal from icodextrin. Conversely, dextrose could be used during the night dwell and icodextrin for the extended daytime dwell in APD systems.

By using separate concentrate sources for each solute, complete individualization of the concentrations and ratios of solutes in the peritoneal dialysate can be achieved. Table 7 provides exemplary ranges of solutes for peritoneal dialysate as made by a system with each solute in a separate concentrate source. With separate concentrate sources for each solute virtually any peritoneal dialysate solution composition can be prepared from a single set of component formulations. The system is useful for patients whose prescriptions change periodically due to diet or other factors. Such patients would need to store multiple formulations if using only one or two concentrate sources, and the risk of errors would be increased.

TABLE 7

| Exemplary dialysate composition from a multi-source system | | | |
| --- | --- | --- | --- |
| Component | Concentration (g/l) | Solution volume (ml/L) | Dialysate composition |
| Part A: Glucose | 850 | 6-53 | 0.55-4.5 g/dL |
| Part B: NaCl | 320 | 15-18 | 132-134 mmol/L |
| Part C: Na Lactate | 1000 | 2-4 | 15-40 mmol/L |
| Part D: MgCl2•6H2O | 500 | 0.2-0.4 | 0.5-1.0 mmol/L |
| Part E: CaCl2•2H2O | 700 | 0.5-1.0 | 2.5-3.5 mmol/L |
| Part F: NaHCO3 | 85 | 0-34 | 0-34 mmol/L |
| Part G: Icodextrin | 1000 | 0-75 | 0-7.5 g/dL |
| Water | | 820-971 | |

In any embodiment of the first or second aspects of the invention, the one or more concentrate sources can be detachable from the rest of the system for sterilization. The concentrate sources can also be sterilized each time the concentrate sources are filled with new concentrate solutions. Further, the concentrate sources can be sterilized after a set number of uses, or after a set period of time. Moreover, the concentrate sources and the rest of the peritoneal dialysate generation system can be sterilized without any of the components by passing a disinfection solution, such as a citric acid, peracetic acid, or bleach solution, through all of the lines and containers of the system.

Figure 3:
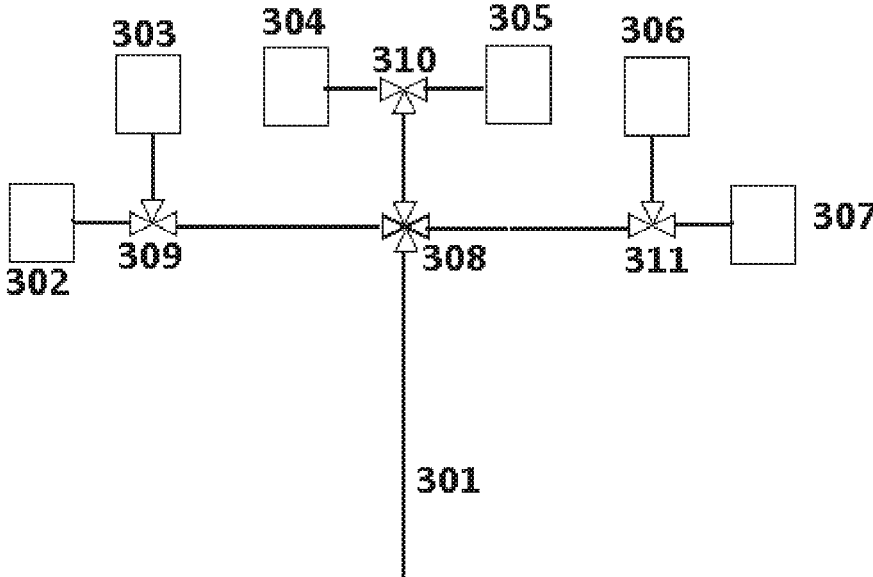
FIG. 3 shows a system for peritoneal dialysate having multiple dialysate containers.

As described, in any embodiment of the first or second aspects of the invention, the system can be configured to generate enough peritoneal dialysate for multiple infusions of peritoneal dialysis into a patient in a single step, such as entire day's requirements of peritoneal dialysate. The peritoneal dialysate generated by the system can be stored in a single dialysate container, and then the patient can use the same peritoneal dialysate container for each exchange of peritoneal dialysate. As illustrated in FIG. 3, the system can be configured to separate portions of peritoneal dialysate into separate dialysate containers, and the patient can use each container only once. Peritoneal dialysate generation flow path 301 can be fluidly connected to a water source, a water purification module, a concentrate source, and a sterilization module, each upstream of dialysate containers 302-307. For clarity, these components are not shown in FIG. 3.

Peritoneal dialysate can be generated through a peritoneal dialysate generation flow path 301 as described herein. The peritoneal dialysate generation flow path 301 can be fluidly connected to a valve 308, which can selectively distribute peritoneal dialysate to each of the dialysate containers 302-307. Valve 308 can be controlled to direct peritoneal dialysate from peritoneal dialysate generation flow path 301 to valve 309. Valve 309 can be controlled to direct the peritoneal dialysate into either of dialysate containers 302 or 303. Once dialysate containers 302 and 303 are filled, valve 308 can be switched to direct the peritoneal dialysate to valve 310. Valve 310 can be controlled to direct the peritoneal dialysate into either of dialysate containers 304 or 305. After filling dialysate containers 304 and 305, valve 308 can be switched to direct peritoneal dialysate to valve 311. Valve 311 can be controlled to direct the peritoneal dialysate to either dialysate container 306 or 307, allowing six separate dialysate containers to be filled with peritoneal dialysate. The patient can then store the generated dialysate in dialysate containers 302-307 until needed. Although six dialysate containers are illustrated in FIG. 3, one of skill in the art will understand that any number of dialysate containers can be used with the systems described herein by modification of the lines and valves. The system can include any number of dialysate containers, including 1, 2, 3, 4, 5, 6, 7, or more dialysate containers. Although illustrated in FIG. 3 as including one four-way valve 308 and three three-way valves 309, 310, and 311, one of skill in the art will understand that several alternative arrangements of valves and fluid lines can selectively fill multiple dialysate containers with the generated peritoneal dialysate. In any embodiment of the first or second aspects of the invention, the dialysate containers 302-307 can be sized to hold dialysate for a single infusion into the patient. In any embodiment of the first or second aspects of the invention, the dialysate containers 302-307 can be sized to hold enough dialysate for multiple infusions of dialysate into the patient. In any embodiment of the first or second aspects of the invention, each dialysate container 302-307 can be between any of 1 and 4 L, 1 and 3 L, 1.5 and 3 L, or 2 and 4 L, storing enough peritoneal dialysate for a single infusion into the patient. In any embodiment of the first or second aspects of the invention, larger or smaller dialysate containers can be used. In any embodiment of the first or second aspects of the invention, the dialysate containers can be between any of 1 and 20 L, 1 and 2 L, 1 and 3 L, 2 and 6 L, 2 and 4 L, 6 and 10 L, 8 and 10 L, 8 and 12 L, 10 and 12 L, 10 to 15 L, or 12 to 20 L. In any embodiment of the first or second aspects of the invention, one or more flow meters (not shown) can be provided for determining the amount of peritoneal dialysate pumped into each dialysate container. A single flow meter can be positioned upstream of valve 308. Multiple flow meters can also be provided between valve 308 and each of valves 309-311. Flow meters can be provided individually for each of the dialysate containers 302-307. A control system (not shown) can be in communication with the flow meters and can be utilized to operate each of the pumps and valves and thereby control the movement of dialysate into each dialysate container.

In any embodiment of the first or second aspects of the invention, different formulations of peritoneal dialysate can be pumped to each of the dialysate containers 302-307. For example, the system can generate peritoneal dialysate for 3-4 day time exchanges and pump the peritoneal dialysate to dialysate containers 302-305. A different formulation of solutes, such as with a different concentration or type of osmotic agent, can be used for an overnight dwell, and the second formulation of peritoneal dialysate can be transferred to dialysate containers 306-307.

Figure 4:
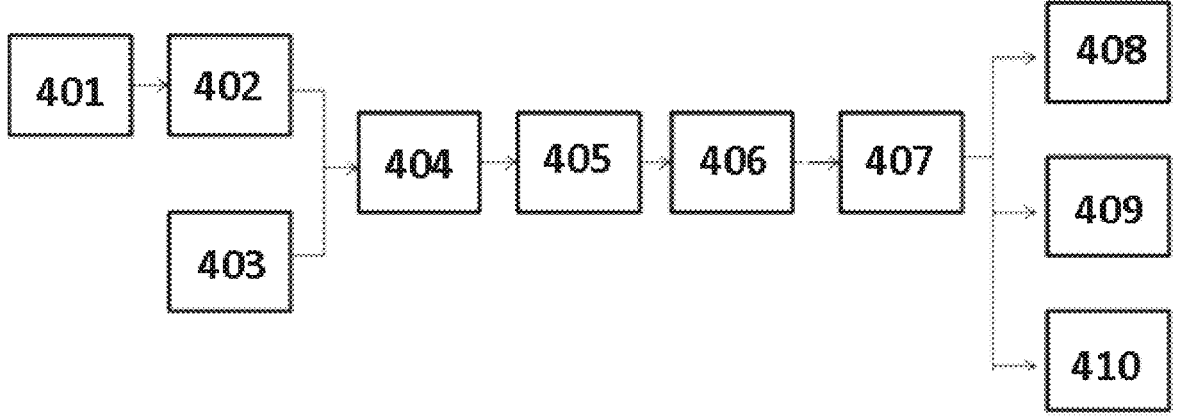
FIG. 4 shows an overview of a system for generating and using peritoneal dialysate with a single concentrate source.

FIG. 4 illustrates an overview of generating peritoneal dialysate in accordance with any embodiment of the first or second aspects of the invention. Water from a water source 401 can be purified by a water purification module 402, as explained. Concentrates from a single concentrate source 403, which can contain both ion concentrates and one or more osmotic agents, can be added to the purified water to generate a non-sterile peritoneal dialysate solution 404. The non-sterile peritoneal dialysate solution 404 is sterilized by a sterilization module 405, which may include an ultrafilter. As explained, the peritoneal dialysate can be further purified by additional components in the sterilization module 406, such as by ultrafiltration with a second ultrafilter, by re circulating the peritoneal dialysate through the same ultra-filter multiple times, or by a UV light source, to generate a sterilized peritoneal dialysate 407. The sterilized peritoneal dialysate 407 can be stored or used by any method described herein, including dispensing an entire day's use of the peritoneal dialysate into a single dialysate container 408, as illustrated in FIG. 1; dispensing the peritoneal dialysate into multiple dialysate containers each large enough for a single treatment 409, as illustrated in FIG. 3, or dispensing the peritoneal dialysate into a single or multiple dialysate containers for immediate use 410.

Figure 5:
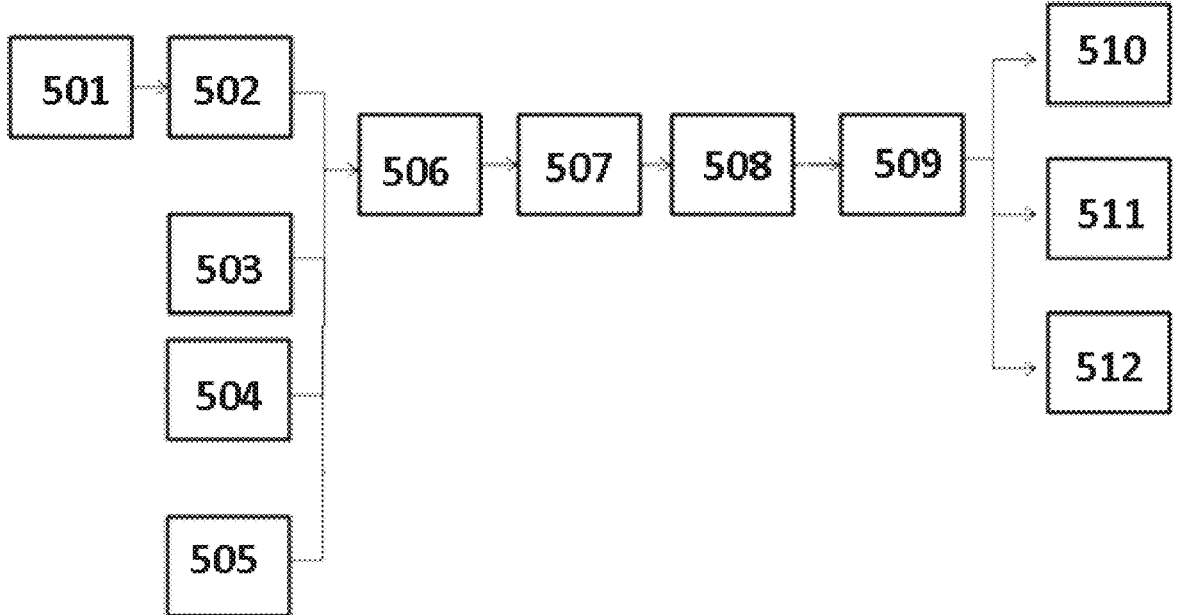
FIG. 5 shows an overview of a system for generating and using peritoneal dialysate with multiple concentrate sources.

FIG. 5 illustrates an overview of generating peritoneal dialysate with multiple concentrate sources. Water from a water source 501 can be purified by a water purification module 502, as explained. Concentrates from an ion concentrate source 503, which can contain sodium, magnesium, calcium, and bicarbonate, as well as any other ions to be used in peritoneal dialysis, can be added to the purified fluid. An osmotic agent, such as dextrose, can be added from a first osmotic agent concentrate source 504. A second osmotic agent, such as icodextrin, can be added from a second osmotic agent concentrate source 505. As illustrated in FIG. 2, any number of concentrate sources can be used for further individualization of the peritoneal dialysate, including separate sources for each of the ions used. After addition of the ion and osmotic agent concentrates, the fluid contains all necessary components for use in peritoneal dialysis as non-sterilized peritoneal dialysate 506. The non-sterile peritoneal dialysate solution 506 can be sterilized by a sterilization module 507, which can include an ultrafilter or other sterilization components. The peritoneal dialysate can be further sterilized by the sterilization module 508, either by ultrafiltration with a second ultrafilter, recirculation through the same ultrafilter, or further sterilized with a UV light source, to generate a sterilized peritoneal dialysate 509. The sterilized peritoneal dialysate 509 can be stored or used by any method described herein, including dispensing an entire days use of the peritoneal dialysate into a single dialysate container 510, as illustrated in FIG. 1; dispensing the peritoneal dialysate into multiple dialysate containers each large enough for a single treatment 511, as illustrated in FIG. 3, or dispensing the peritoneal dialysate into a single or multiple dialysate containers for immediate use 512.

Figure 6:
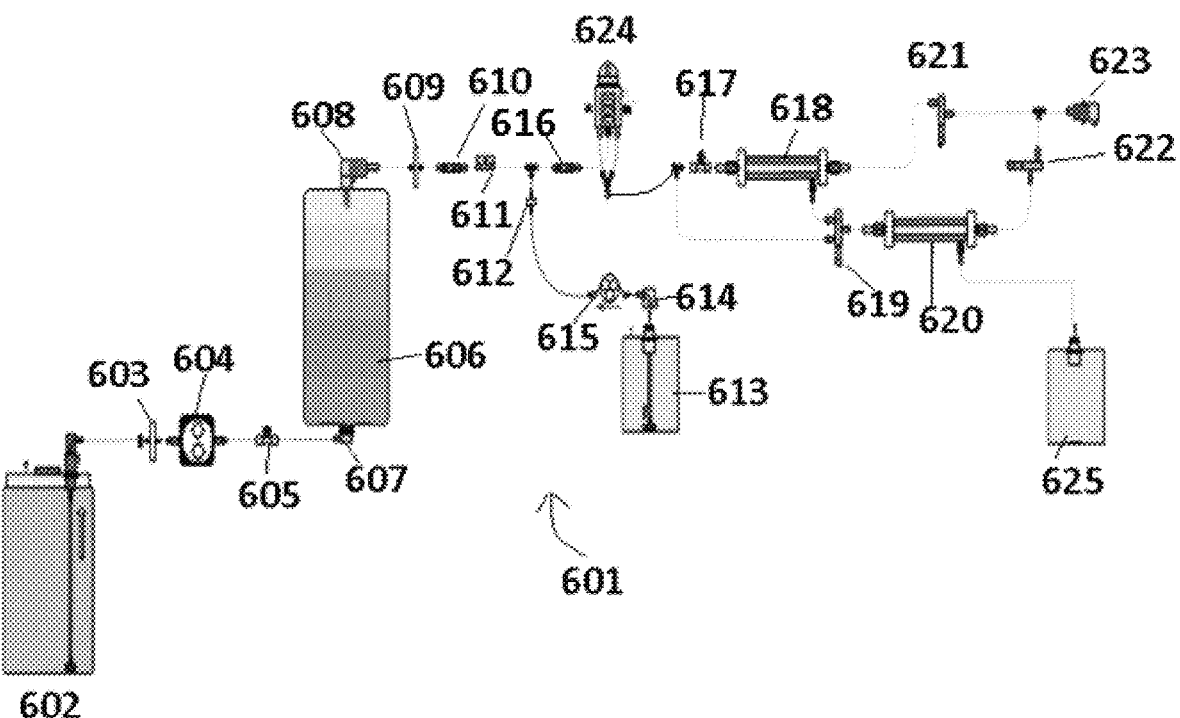
FIG. 6 shows an alternative flow path for generating peritoneal dialysate.

FIG. 6 illustrates an alternative peritoneal dialysate generation flow path 601. Water from a water source 602 can be pumped through filter 603 by system pump 604. The filter 603 can remove any particulate matter from the water prior to entering the peritoneal dialysate generation flow path 601. Pressure sensor 605 measures the pressure of the incoming water to ensure the pressure within the peritoneal dialysate generation flow path 601 is within predetermined ranges. The water can then be pumped through a water purification module, illustrated as a sorbent cartridge 606 in FIG. 6. As described, the water purification module can alternatively or additionally include activated carbon, a reverse osmosis module, a carbon filter, an ion exchange resin, and/or a nanofilter. The water enters the sorbent cartridge 606 through sorbent cartridge inlet 607 and exits through sorbent cartridge outlet 608. Filter 609 removes any particulate matter in the fluid after exiting sorbent cartridge 606. A conductivity sensor 610 determines the conductivity of the fluid exiting sorbent cartridge 606 to ensure the water has been purified. Flow sensor 611 determines the flow rate of the fluid exiting sorbent cartridge 606. To generate peritoneal dialysate, concentrates can be added from concentrate source 613 through concentrate connector 614 by concentrate pump 615. Although shown as a single concentrate source 613 in FIG. 6, concentrates can be added from two or more concentrate sources wherein at least one concentrate source is a source for independently providing glucose to separately control addition of osmotic agents such as glucose. Concentrate filter 612 removes any particulate matter from the concentrate before entering the peritoneal dialysate generation flow path 601. A conductivity sensor 616 determines the conductivity of the generated peritoneal dialysate after addition of the concentrates to ensure the peritoneal dialysate has the correct solute concentrations. Pressure sensor 617 measures the fluid pressure prior to the fluid entering the sterilization module, shown as ultrafilters 618 and 620. pH sensor 624 can determine the pH of the peritoneal dialysate to ensure the peritoneal dialysate has a proper pH.

As described, the peritoneal dialysate is sterilized by pumping the peritoneal dialysate through a sterilization module which can include a first ultrafilter 618, and optionally a second ultrafilter 620. Valves 621 and 622, as well as connector 623 are used in disinfection and backflushing of the ultrafilters. The fluid can then be pumped into dialysate container 625 for storage until needed by the patient. As described, the system can include any number of dialysate containers, and is not limited to the single dialysate container 625 illustrated in FIG. 6. Valves 621 and 622, as well as three way valve 619 allow for back flushing of the ultrafilters 618 and 620 during disinfection.

Figure 7A:
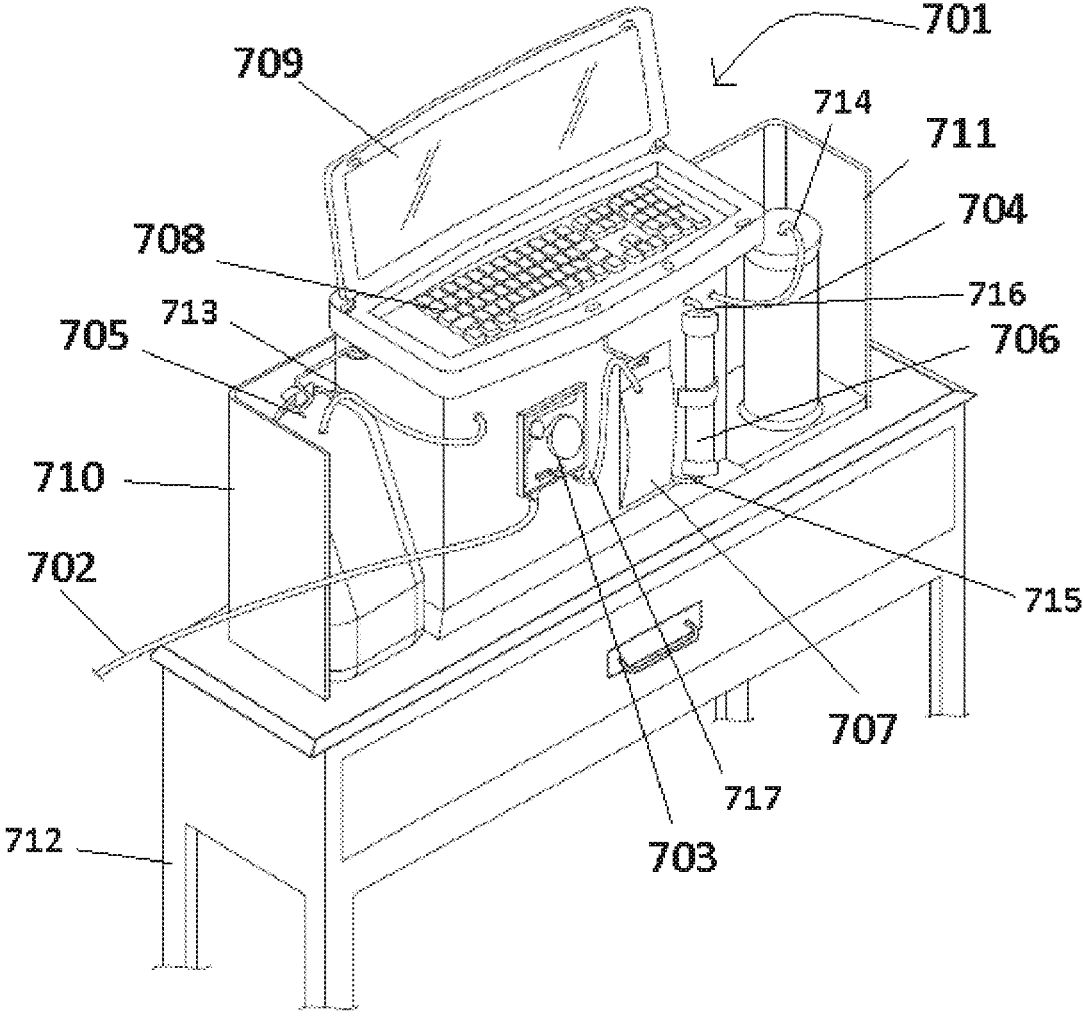
FIG. 7A shows a perspective view of a peritoneal dialysate generation cabinet with a bag as a dialysate container.
Figure 7B:
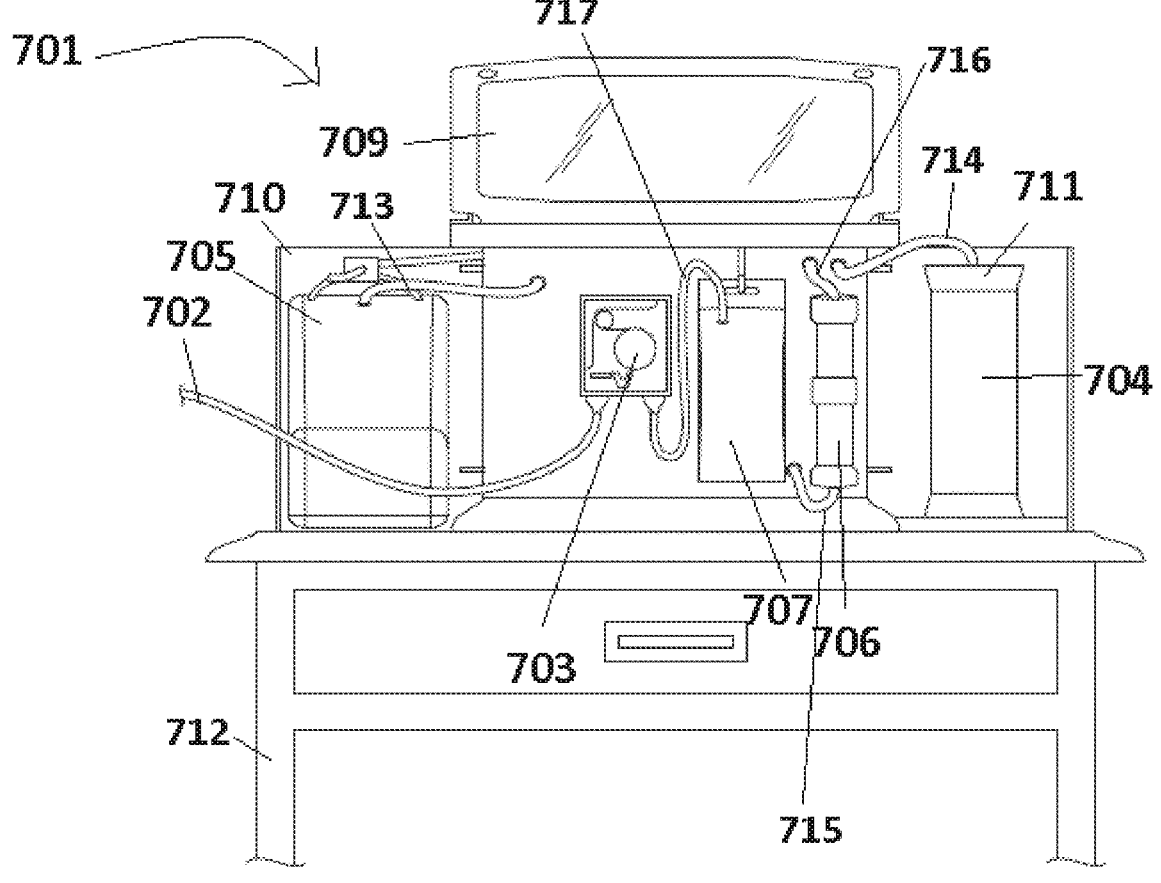
FIG. 7B shows a front view of a peritoneal dialysate generation cabinet with a bag as a dialysate container.
Figure 7C:
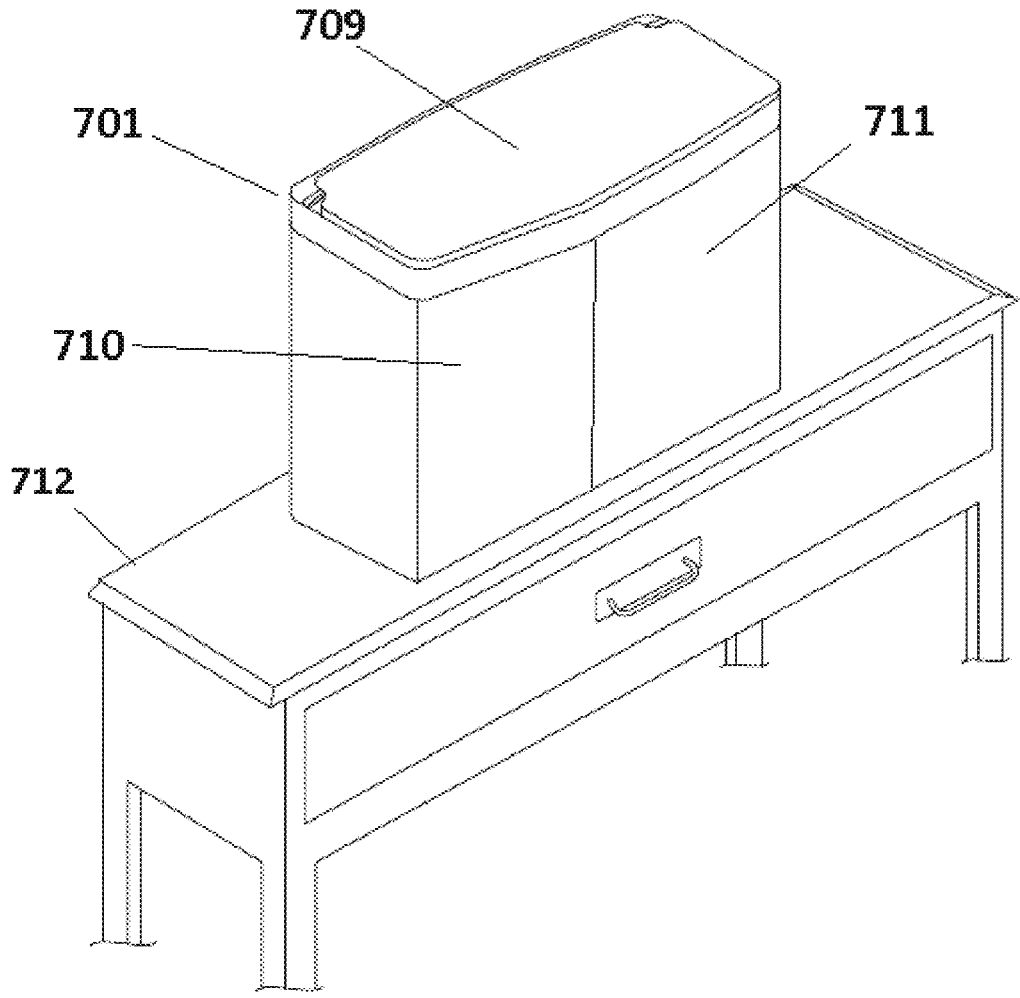
FIG. 7C shows a peritoneal dialysate generation cabinet with the doors shut.

FIGS. 7A-C illustrate a non-limiting embodiment of a peritoneal dialysate generation cabinet 701. FIG. 7A illustrates a perspective view of the peritoneal dialysate generation cabinet 701, while FIG. 7B illustrates a front view of the peritoneal dialysate generation cabinet 701. FIG. 7C shows the peritoneal dialysate generation cabinet 701 with door panels closed. A fluid line 702 can connect a water source to the peritoneal dialysate generation cabinet 701. System pump 703 provides a driving force for the movement of fluid throughout the peritoneal dialysate generation flow path. The water is pumped through the peritoneal dialysate generation cabinet 701 to a water purification module, shown as sorbent cartridge 704 in FIG. 7. The water enters the sorbent cartridge 704 through tubing (not shown) connected to the bottom of the sorbent cartridge through the base of the peritoneal dialysate generation cabinet 701, and exits through tubing 714 at a top of the sorbent cartridge. Concentrates from concentrate source 705 are added to the fluid through tubing 713 as described to generate non-sterilized peritoneal dialysate. A concentrate pump (not shown) can provide a driving force to move fluid from the concentrate source 705 into the peritoneal dialysate generation flow path inside of the peritoneal dialysate generation cabinet 701. The generated peritoneal dialysate can then be pumped through a sterilization module, shown as ultrafilter 706, for sterilization. The peritoneal dialysate enters the ultrafilter 706 through tubing 715 in a base of the ultrafilter 706 and exits through tubing 716 at a top of the ultrafilter 706. A second ultrafilter and/or a UV light source (not shown in FIG. 7) can also be included. The peritoneal dialysate can then be pumped through dialysate line 717 into a dialysate container, shown as bag 707, for storage until used by the patient. As described, the peritoneal dialysate generation flow path can include various sensors for detection of conductivity, pH, refractive index, or other dialysate parameters. The sensors can be included either inside or outside of the body of the peritoneal dialysate generation cabinet 701. The fluid lines and valves connecting the components of the peritoneal dialysate generation flow path can likewise be positioned inside of the cabinet body. As described, peritoneal dialysate generation cabinet 701 can have a graphical user interface including screen 709 and keyboard 708. Messages from the control system to the user, or from the user to the control system, can be generated and read through the graphical user interface. The user can direct the generation of peritoneal dialysate through keyboard 708, and can receive messages from the system through screen 709. The system can generate alerts to the user, including any problems detected by any of the sensors, as well as the progress of peritoneal dialysate generation. Any type of user interface can be used in place of the keyboard 708 and screen 709 in FIGS. 7A-C. Alternatively, other interfaces can be included, such as lights, dials, buttons, switches or the like. In any embodiment, a single button can be used for directing the generation of peritoneal dialysate in place of the keyboard. In any embodiment, either keyboard 708 or screen 709 can be used alone, as with a single touch screen for both data entry and display to enable simple operation.

When not in use, the concentrate source 705, the sorbent cartridge 704, and dialysate bag 707 can be removed, and the doors 710 and 711 of the peritoneal dialysate generation cabinet 701 can be closed to minimize the space required as shown in FIG. 7C. Additionally, the screen 709 can be folded down into the top of the peritoneal dialysate generation cabinet 701, further minimizing the space needed. The doors can be open and closed by any method known in the art, including magnets, handles, indentations, hooks, or any other method of opening and closing the doors. The peritoneal dialysate generation cabinet 701 can have a small size and portability optimized for in-home or beside use. Although shown on table 712, the peritoneal dialysate generation cabinet 701 can be used on any stable flat surface.

Figure 8:
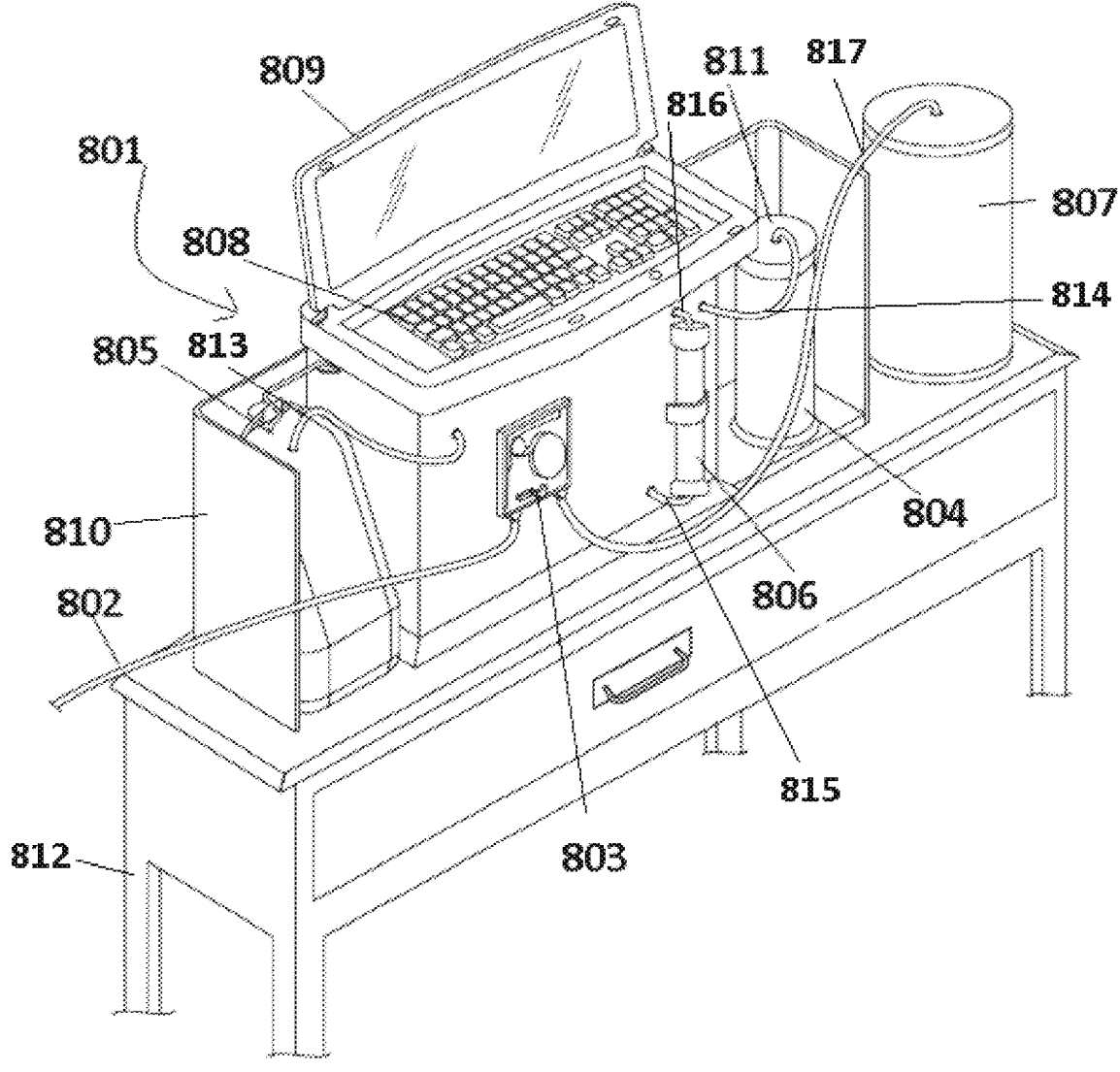
FIG. 8 shows a peritoneal dialysate generation cabinet with a reusable dialysate container.

FIG. 8 illustrates a similar cabinet 801 to the system of FIG. 7, with a reusable dialysate container, shown as stainless steel container 807. A fluid line 802 can connect a water source to the cabinet 801. System pump 803 provides a driving force for the movement of fluid throughout a peritoneal dialysate generation flow path. The water can be pumped through the cabinet 801 to a water purification module, shown as sorbent cartridge 804 in FIG. 8. The water enters the sorbent cartridge 804 through tubing (not shown) connected to the bottom of the sorbent cartridge 804 through the base of the cabinet 801. Concentrates from concentrate source 805 are added to the fluid as described to generate non-sterilized peritoneal dialysate. A concentrate pump (not shown) can provide a driving force to move fluid from the concentrate source 805 into the peritoneal dialysate generation flow path inside of the cabinet 801. The generated peritoneal dialysate can then be pumped through a sterilization module, shown as ultrafilter 806 for sterilization. A second ultrafilter or UV light source (not shown in FIG. 8) can also be included. The peritoneal dialysate can then be pumped into a dialysate container, shown as a reusable dialysate container 807 in FIG. 8, for storage until use. As described, the peritoneal dialysate generation flow path can include various sensors for detection of conductivity, pH, refractive index, or other dialysate parameters. The sensors can be included either inside or outside of the body of the cabinet 801. The fluid lines and valves connecting the components of the peritoneal dialysate generation flow path can likewise be positioned inside of the cabinet body. As described, cabinet 801 can have a graphical user interface including screen 809 and keyboard 808. The user can direct the generation of peritoneal dialysate through keyboard 808, and can receive messages from the system through screen 809.

Figure 9A:
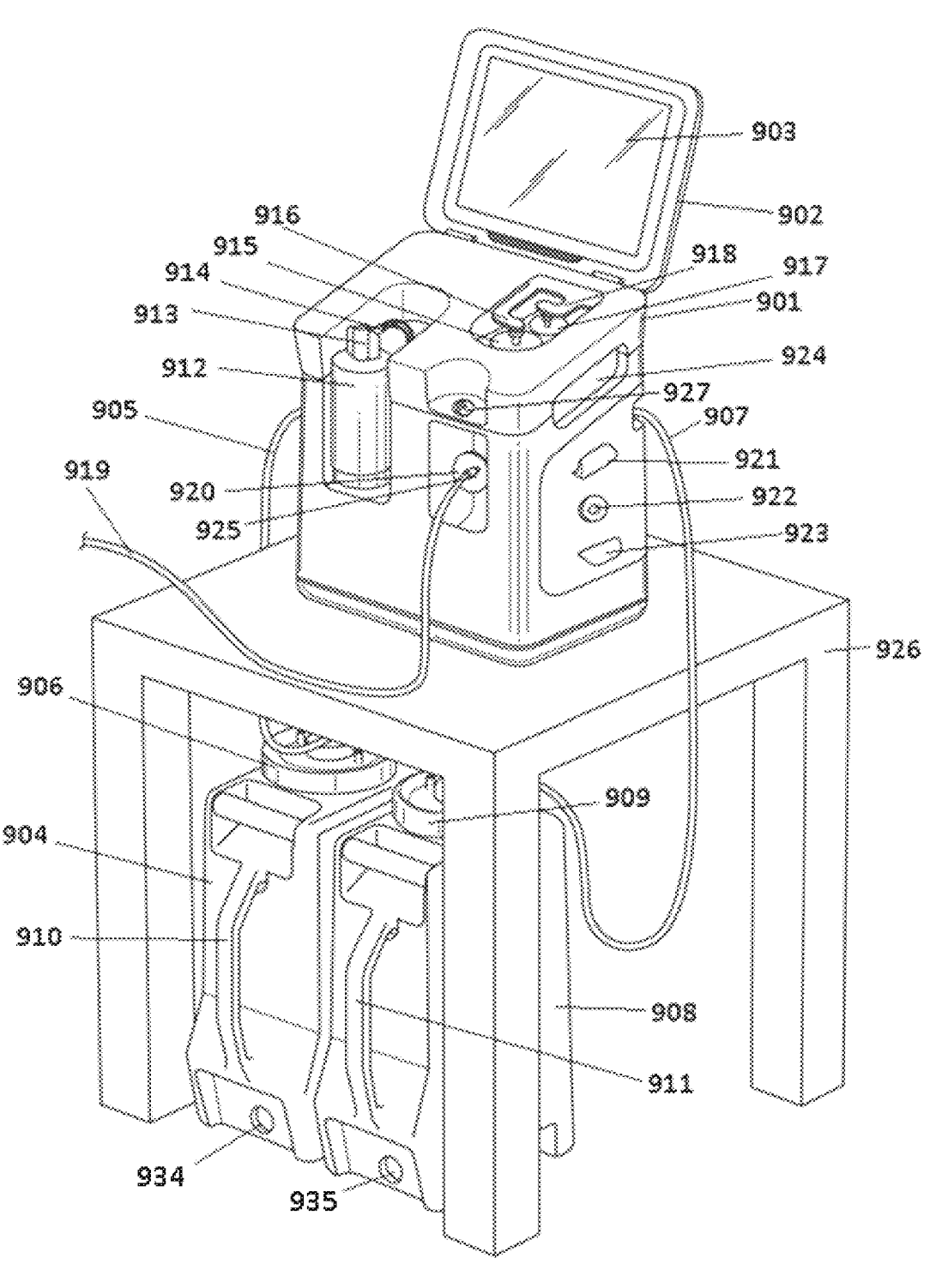
FIGS. 9A-D show a peritoneal dialysate generation cabinet for generation of peritoneal dialysate.
Figure 9B:
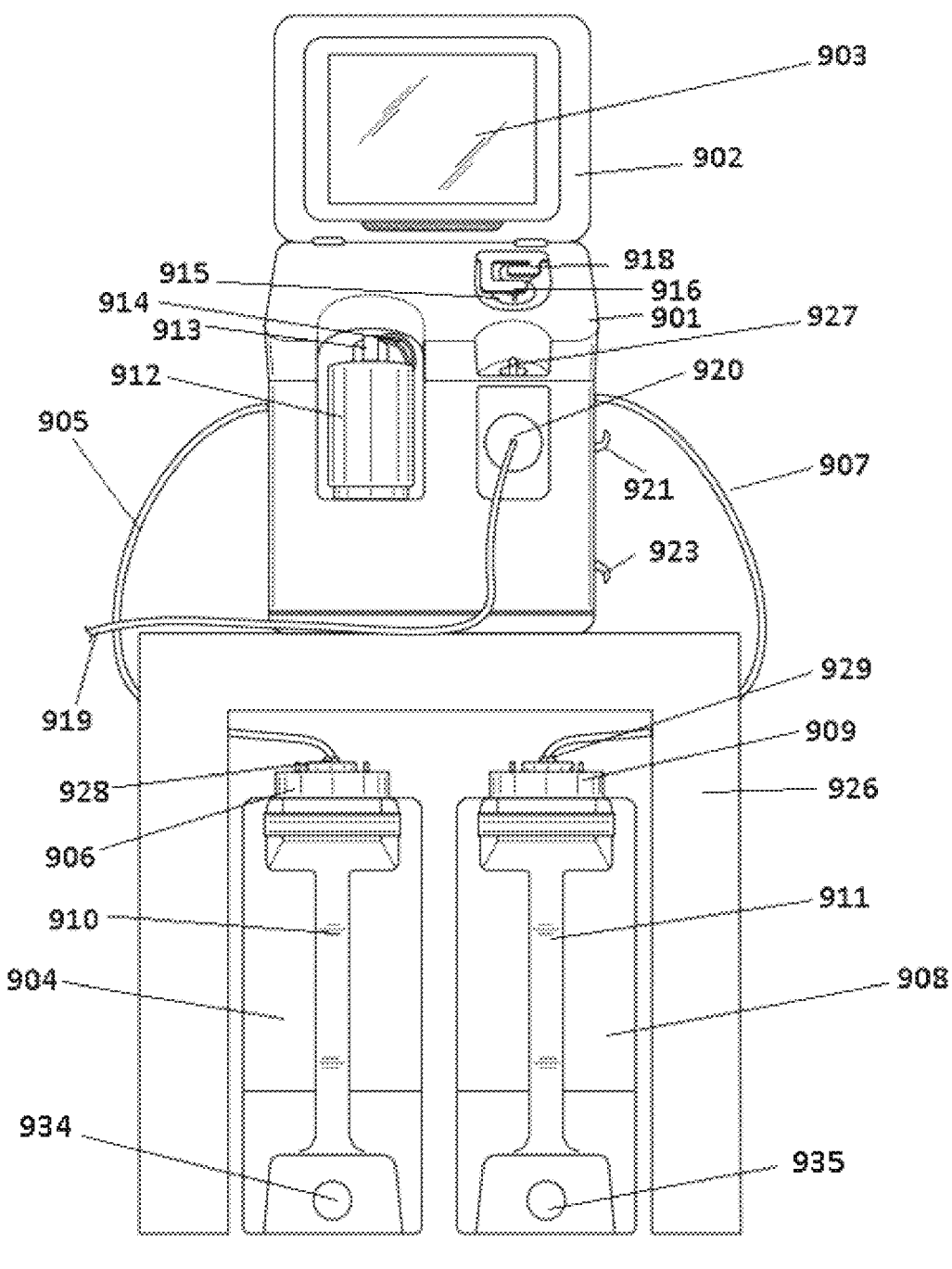
Figure 9C:
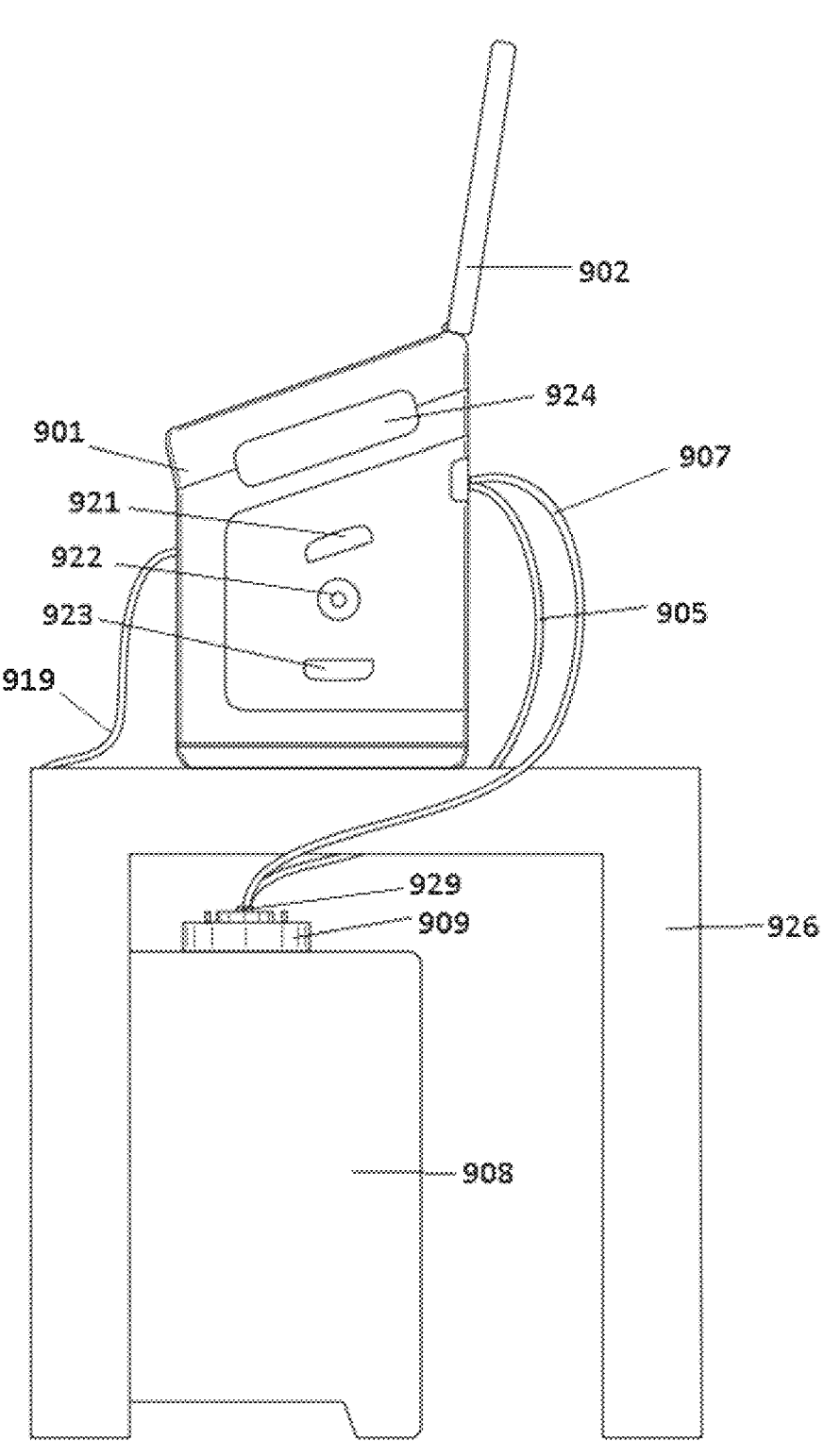
Figure 9D:
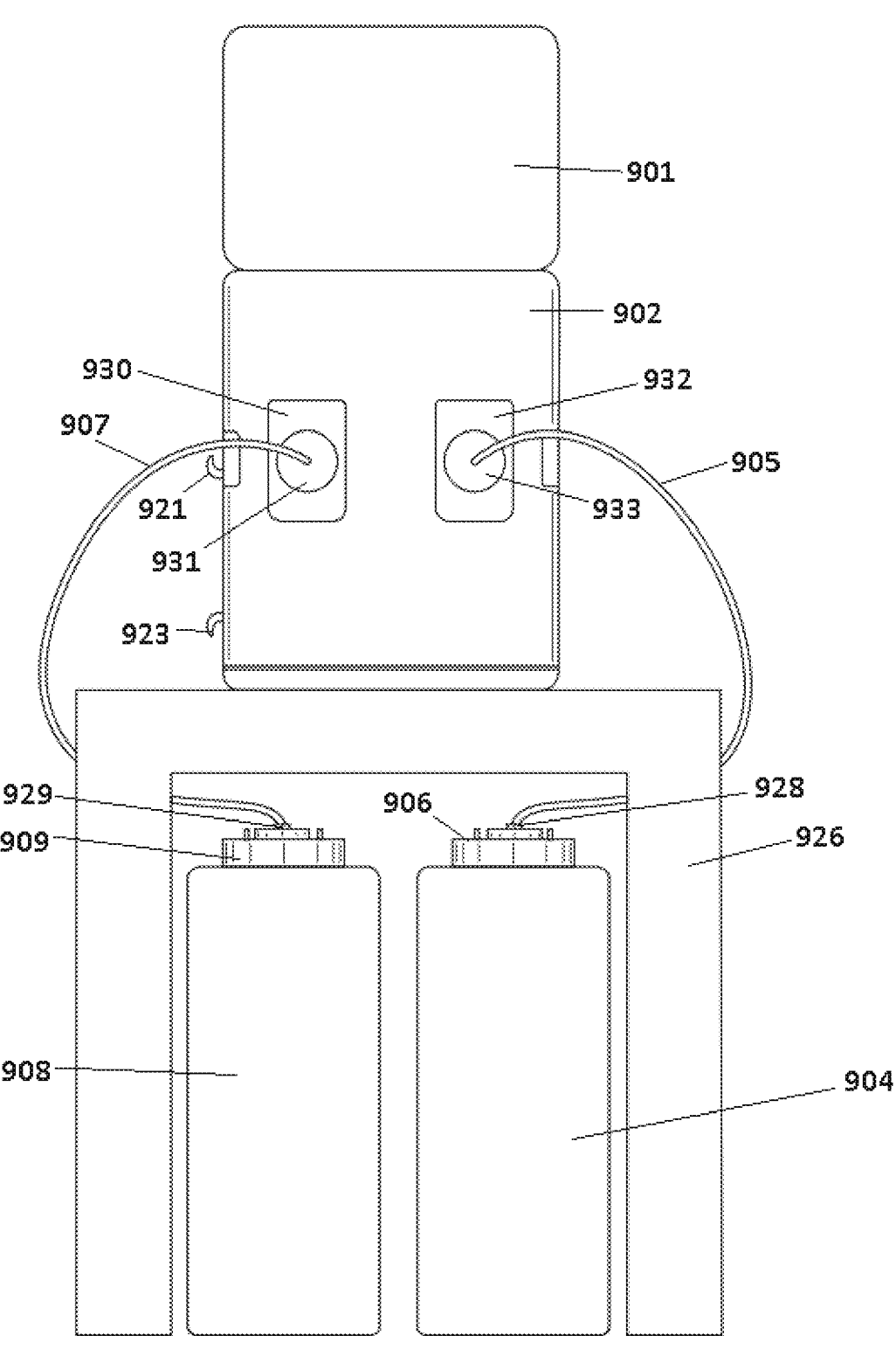

FIGS. 9A-D illustrate a non-limiting embodiment of the peritoneal dialysate generation system arranged as a peritoneal dialysate generation cabinet 901. FIG. 9A illustrates a perspective view of the peritoneal dialysate generation cabinet 901, FIG. 9B illustrates a front view of the peritoneal dialysate generation cabinet 901, FIG. 9C illustrates a side view of the peritoneal dialysate generation cabinet 901, and FIG. 9D illustrates a back view of the peritoneal dialysate generation cabinet 901.

A fluid line 905 can connect a water source 904 to the peritoneal dialysate generation cabinet 901. The fluid line 905 can enter through a connector 928 in a top 906 of the water source 904. The fluid line 905 connects to the peritoneal dialysate generation flow path as described with reference to FIGS. 1-3 and 6, through a back of the peritoneal dialysate generation cabinet 901 through connector 932 having a fitting 933 for holding the fluid line 905, as illustrated in FIG. 9D. Any of the fluid lines illustrated can be disconnected and removed from the system for cleaning and replacement. A pump (not shown) can provide a driving force for the movement of fluid throughout the peritoneal dialysate generation flow path if required. Water is pumped through the peritoneal dialysate generation cabinet 901 to a water purification module, shown as sorbent cartridge 912 in FIGS. 9A-B. The water can enter the sorbent cartridge 912 through tubing (not shown) connected to a bottom of the sorbent cartridge 912 within the peritoneal dialysate generation cabinet 901. The water exits the sorbent cartridge 912 through connector 913 and tubing 914. An osmotic agent from osmotic agent source 915 and an ion concentrate from an ion concentrate source 917 are added to the fluid as described to generate non-sterilized peritoneal dialysate. The osmotic agent concentrate is added to the fluid through a connector shown as paddle connector 916. The ion concentrate is added to the fluid through paddle connector 918. A concentrate pump (not shown) can provide a driving force to move fluid from the concentrate sources into the peritoneal dialysate generation flow path inside of the peritoneal dialysate generation cabinet 901. As described, the system can use a single ion concentrate source in place of the two sources shown in FIG. 9A-B, or more than two concentrate sources. The generated peritoneal dialysate can then be pumped through a sterilization module (not shown), such as an ultrafilter. A second ultrafilter and/or a UV light source can also be included. The peritoneal dialysate can then be pumped into dialysate line 919 through connector 920 and into a dialysate container (not shown in FIGS. 9A-D), for storage until used by the patient, or into a non-integrated cycler for immediate use by the patient. Fitting 925 allows the dialysate line 919 to be removed from the system for cleaning or replacement. Waste fluids can be pumped out of the system through waste line 907, which connects to the peritoneal dialysate generation cabinet 901 through connector 930 having fitting 931. The waste line 907 enters waste container 908 through a connector 929 in the top 909 of the waste container 908. Handles 910 and 911 can be included on water source 904 and waste container 908 for easy movement and storage. Although the peritoneal dialysate generation cabinet 901 is illustrated on top of table 926 in FIGS. 9A-D, the peritoneal dialysate generation cabinet 901 can be used on any stable flat surface.

As described, the peritoneal dialysate generation flow path can include various sensors for detection of conductivity, pH, refractive index, or other dialysate parameters. The sensors can be included either inside or outside of the body of the peritoneal dialysate generation cabinet 901. The fluid lines and valves connecting the components of the peritoneal dialysate generation flow path can likewise be positioned inside of the cabinet body. As described, a top of the peritoneal dialysate generation cabinet 901 can have a graphical user interface 902 including screen 903. Messages from the control system to the user, or from the user to the control system, can be generated and read through the graphical user interface. The user can direct the generation of peritoneal dialysate through the graphical user interface 902, and can receive messages from the system through screen 903. The system can generate alerts to the user, including any problems detected by any of the sensors, as well as the progress of peritoneal dialysate generation. A handle 924 can be included for opening the peritoneal dialysate generation cabinet 901 to allow access to components on the inside of the cabinet. Handles 921 and 923 can be included to hold the fluid lines and power cord when not in use.

Disinfection connector 922 illustrated in FIGS. 9A and 9C can be included for disinfection of the waste line 907. During disinfection, the waste line 907 can be disconnected from waste container 908 and connected to disinfection connector 922. Disinfectant solution from a disinfectant source (not shown in FIGS. 9A-D) can then be circulated through the waste line 907 to disinfect the waste line 907. Disinfection connector 927 can be included for disinfection of fluid line 905. Fluid line 905 can be connected to disinfection connector 922 and disinfection solution can be circulated through the fluid line 905. Drain 934 on water source 904 and drain 935 on waste container 908, allow the water source 904 and waste container 908 to be drained without inverting the containers.

Figure 10:
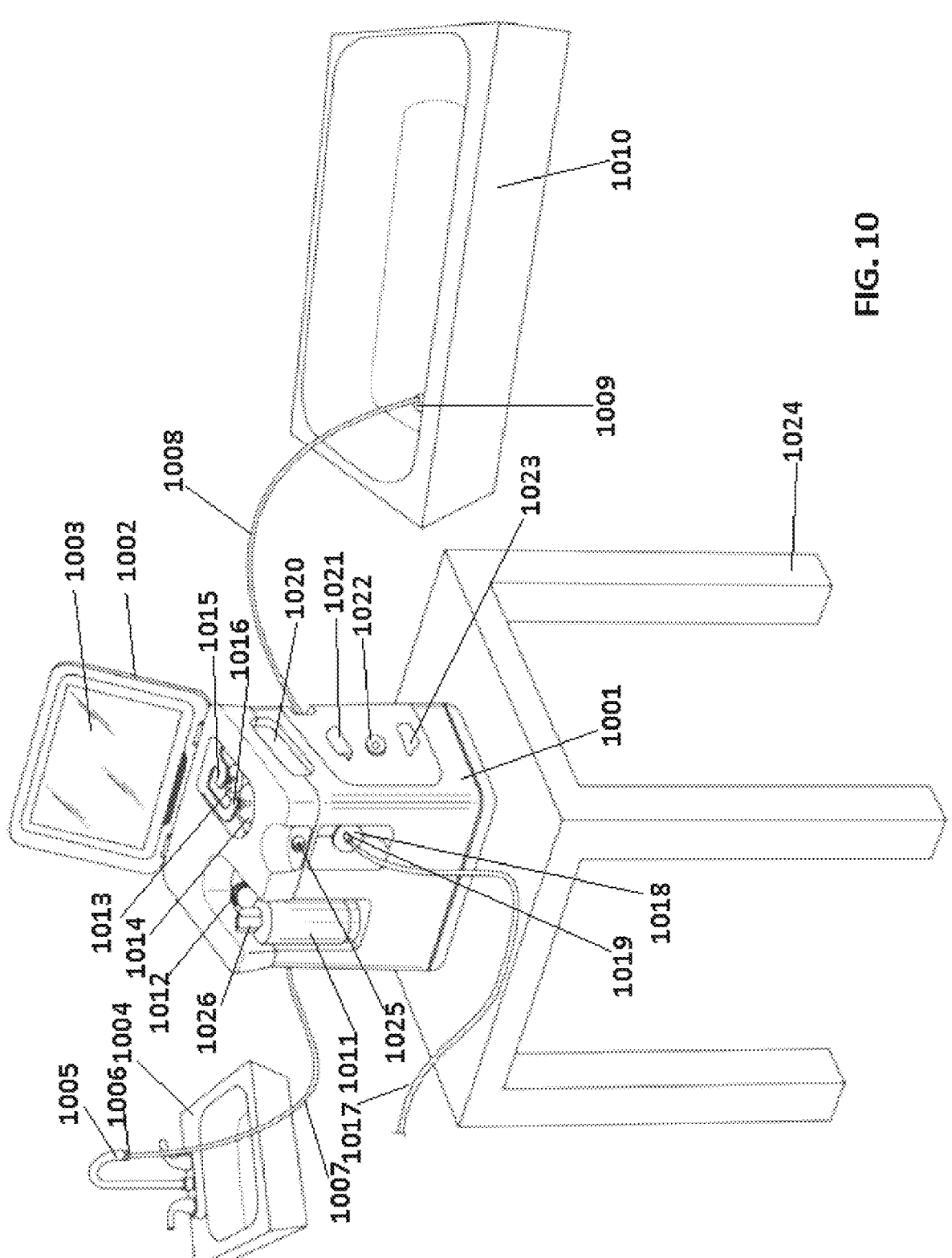
FIG. 10 shows a peritoneal dialysate generation cabinet connected to a sink and drain.

FIG. 10 illustrates a peritoneal dialysate generation cabinet 1001 using a non-purified water source, faucet 1005 in sink 1004. Although illustrated as faucet 1005 and sink 1004, one of ordinary skill in the art will understand that any water source can be used. The ability to use municipal or other non-purified sources of water allow the peritoneal dialysate generation system to work at a patient's home without the need to store large amounts of purified water or dialysate. Fitting 1006 connects the water line 1007 to the faucet 1005 or other water source, allowing the water line 1007 to be connected or disconnected as necessary. A pump (not shown) provides a driving force for the movement of fluid throughout the peritoneal dialysate generation flow path. The water is pumped through the peritoneal dialysate generation cabinet 1001 to a water purification module, shown as sorbent cartridge 1011 in FIG. 10. The water enters the sorbent cartridge 1011 through tubing (not shown) connected to the bottom of the sorbent cartridge within the peritoneal dialysate generation cabinet 1001. The water exits the sorbent cartridge 1011 through connector 1026 and tubing 1012. An osmotic agent from osmotic agent source 1013 and an ion concentrate from an ion concentrate source 1014 are added to the fluid as described to generate non-sterilized peritoneal dialysate. The osmotic agent concentrate is added to the fluid through a connector shown as paddle connector 1016. The ion concentrate is added to the fluid through paddle connector 1015. A concentrate pump (not shown) can provide a driving force to move fluid from the concentrate sources into the peritoneal dialysate generation flow path inside of the peritoneal dialysate generation cabinet 1001. As described, the system can use a single ion concentrate source in place of the two sources shown in FIG. 10, or more than two concentrate sources. The generated peritoneal dialysate can then be pumped through a sterilization module (not shown), such as an ultrafilter. A second ultrafilter and/or a UV light source can also be included. The peritoneal dialysate can then be pumped into dialysate line 1017 through connector 1018 and into a dialysate container (not shown in FIG. 10), for storage until used by the patient, or into a non-integrated cycler for immediate use by the patient. Fitting 1019 allows the dialysate line 1017 to be removed from the system for cleaning or replacement. Waste fluids can be pumped out of the system through waste line 1008, which can connect to a drain 1009 shown in bathtub 1010. Although shown as a bathtub drain 1009 in FIG. 10, the waste fluids can be conveyed to any type of drain, or alternatively to a waste container as illustrated in FIGS. 9A-D. Although the peritoneal dialysate generation cabinet 1001 is illustrated on top of table 1024 in FIG. 10, the peritoneal dialysate generation cabinet 1001 can be used on any stable flat surface. In certain embodiments, the peritoneal dialysate generation cabinet 1001 and dialysate container or non-integrated cycler can be used in the same room as the water source and drain 1009. Alternatively, a non-integrated cycler or dialysate container can be placed in a separate room, with tubing long enough to reach the non-integrated cycler or dialysate container. For longer distances, the tubing should be strong enough to withstand the pressures necessary in pumping fluid over longer distances.

As described, a top of the peritoneal dialysate generation cabinet 1001 can have a graphical user interface 1002 including screen 1003. Messages from the control system to the user, or from the user to the control system, can be generated and read through the graphical user interface. The user can direct the generation of peritoneal dialysate through the graphical user interface 1002, and can receive messages from the system through screen 1003. The system can generate alerts to the user, including any problems detected by any of the sensors, as well as the progress of peritoneal dialysate generation. A handle 1020 can be included for opening the peritoneal dialysate generation cabinet 1001 to allow access to components on the inside of the cabinet. Handles 1021 and 1023 can be included to hold the fluid lines and power cord when not in use.

Disinfection connector 1022 can be included for disinfection of the waste line 1008. During disinfection, the waste line 1008 can be disconnected from the drain 1009 and connected to disinfection connector 1022. Disinfectant solution from a disinfectant source (not shown in FIG. 10) can then be circulated through the waste line 1008 to disinfect the waste line 1008. Disinfection connector 1025 can be included for disinfection of water line 1007. The water line 1007 can be disconnected from faucet 1005 and connected to disinfection connector 1025. Disinfectant solution can be circulate through the water line 1007 for disinfection.

Figure 11:
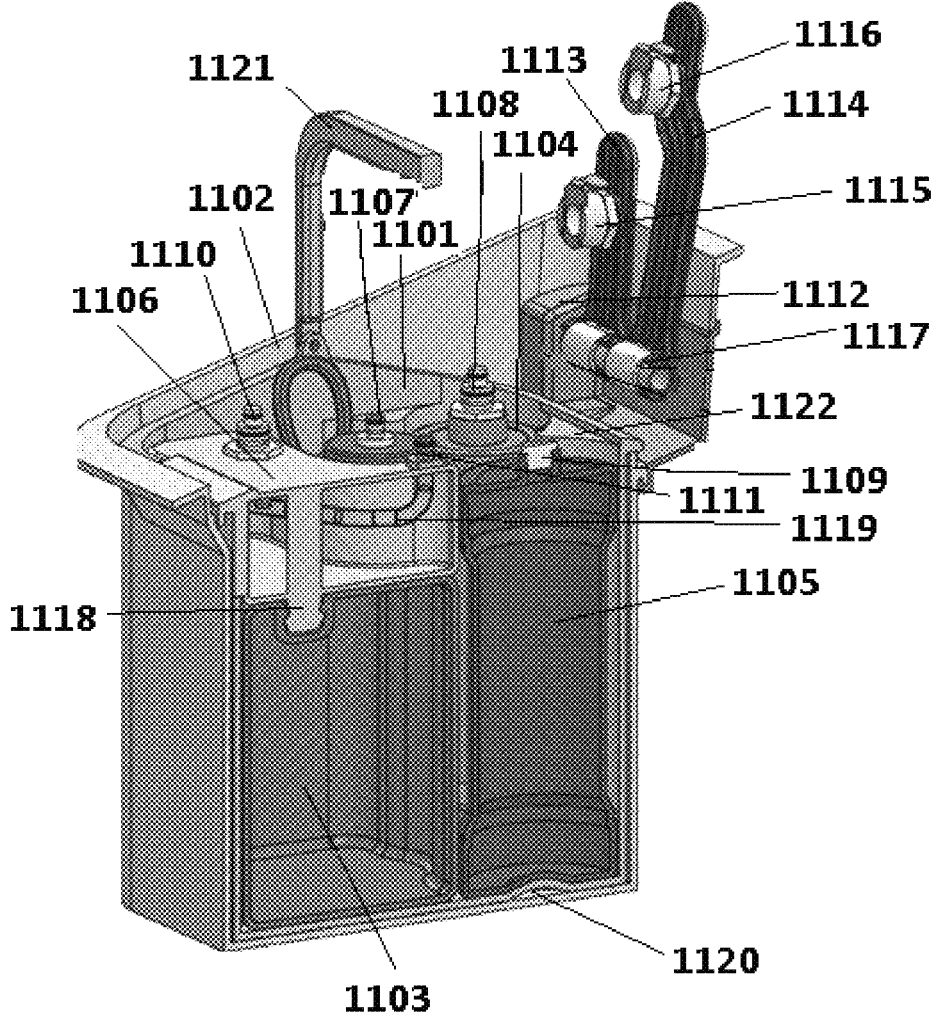
FIG. 11 shows a dialysis caddy for use in a peritoneal dialysate generation flow path.

In any embodiment of the first, second, or third aspects of the invention, the solute sources included in the dialysate generation module can be provided in a dialysis caddy. A dialysis caddy is a container adapted to contain one or more other containers, each having one or more solute sources. One non-limiting example of a dialysis caddy is shown in FIG. 11. The dialysis caddy 1101 can contain some or all of the solute sources necessary for peritoneal dialysis. In any embodiment of the first or second aspects of the invention, the dialysis caddy 1101 can contain an ion concentrate source 1103, osmotic agent source 1104, and sodium chloride source 1105. As explained, the ion concentrate source 1103 can contain any one or more of ion concentrates, such as magnesium chloride, calcium chloride or potassium chloride, or any other solutes used in peritoneal dialysis. Osmotic agent source 1104 can contain one or more osmotic agents, such as glucose, dextrose, or icodextrin. One of skill in the art will understand that any of the solutes can be contained in separate sources, and that the dialysis caddy 1101 can be adapted for any number of concentrate sources. In use, the dialysis caddy 1101 can be placed in a receiving slot of a dialysis system 1102. As shown in FIG. 11, the dialysis caddy 1101 can be configured so each of the ion concentrate source 1103, osmotic agent source 1104, and sodium chloride source 1105 are aligned with connectors for connection to the peritoneal dialysate generation flow path, such as the connectors on paddle assemblies 1113 and 1114. In any embodiment of the first or second aspect of the invention, the dialysis caddy 1101 can also contain a disinfectant source 1106, which may contain a disinfectant, such as citric acid. To disinfect the system, the dialysis caddy 1101 can be turned so container connectors 1110 and 1111 on the disinfectant source 1106 can connect to the connectors on paddle assemblies 1113 and 1114.

If dialysis caddy 1101 is configured to generate peritoneal dialysate, container connector 1107 on ion concentrate source 1103 and container connector 1108 on osmotic agent source 1104 can connect to caddy connectors 1115 on paddle assembly 1113 and caddy connector 1116 on paddle assembly 1114. Container connector 1109 on sodium chloride source 1105 can also connect to a caddy connector (not shown in FIG. 11). The paddles can form a part of a paddle assembly 1112. To connect the sources to the paddles, the paddles can be rotated downward on hinge 1117 and the caddy connectors 1115 and 1116 can connect to ion concentrate source 1103 and osmotic agent source 1104 respectively. In any embodiment of the first or second aspects of the invention, as shown in FIG. 11, the dialysis caddy 1101 and the sources within the caddy have one or more fitting feature to ensure the sources are connected to the correct paddle. The fitting features can also have the additional benefit of ensuring a tight fit within the dialysis caddy 1101, and resist inadvertent movement. The one or more fitting features can ensure each source occupies a unique position within the dialysis caddy 1101. Moreover, in any embodiment, the interior of the dialysis caddy 1101 can itself be a shaped fitting feature so each source can only be placed within a specific position or receiving compartment within the dialysis caddy 1101. In any embodiment of the first or second aspects of the invention, fitting features can be included on any connection surface of the caddy, where any source contacts the interior of the caddy. The shape of a caddy surface can include fitting feature protrusion 1120, which is a protrusion on the base of the dialysis caddy 1101. The base of sodium chloride source 1105 can be designed with a corresponding complementary indentation, such as a similarly sized recess, while the other sources lack the complimentary indentation. Sodium chloride source 1105 will be the only source that can properly fit into the position in the caddy above the fitting feature of protrusion 1120. Similarly, fitting feature protrusion 1122 is a protrusion in the side of the dialysis caddy 1101 interior. The protrusion 1122 separates the sidewall of the dialysis caddy 1101 interior into two sections. Osmotic agent source 1104 can be the only source with the proper size, shape, or geometry to fit within one of the sections on the sidewall, whereas sodium chloride source 1105 can be the only source with the proper size, shape, or geometry to fit within the other section. Each concentrate source can be positioned in one particular location within the dialysis caddy 1101. In any embodiment, the concentrate sources themselves can have fitting features to ensure the proper arrangement of the concentrate sources within the dialysis caddy 1101. In FIG. 11 disinfectant (e.g. citric acid) source 1106 includes flange 1118. Ion concentrate source 1103 has a corresponding slot. The disinfectant (e.g. citric acid) source 1106 can only be placed within the dialysis caddy 1101 at the precise position above ion concentrate source 1103. By sizing and shaping the interior of the cavity and the concentrate sources, the concentrate sources can only be placed within the dialysis caddy 1101 in a single arrangement. If the dialysis caddy 1101 is attached to the rest of the dialysis system 1102, the concentrate sources and connectors line up with the proper paddles for connection to the dialysis system. The alignment ensures the proper solutes from the concentrate sources enter the dialysate flow path at the correct locations, and that the proper pumps and valves are controlling the correct solute additions. In any embodiment of the first or second aspects of the invention, handle 1121 can be included for easy of carrying and removal of the dialysis caddy 1101 from the dialysis system 1102. During use, fluid lines, such as line 1119 in disinfectant (e.g. citric acid) source 1106, can move fluids from the concentrate sources into the paddles.

Alternatively, any method of loading the peritoneal dialysate concentrates can be included in the described systems. For example, the peritoneal dialysate concentrates can be added using a disposable cassette. The disposable cassette can be multi-use or single-use with disposal of the cassette after therapy.

Figure 12:
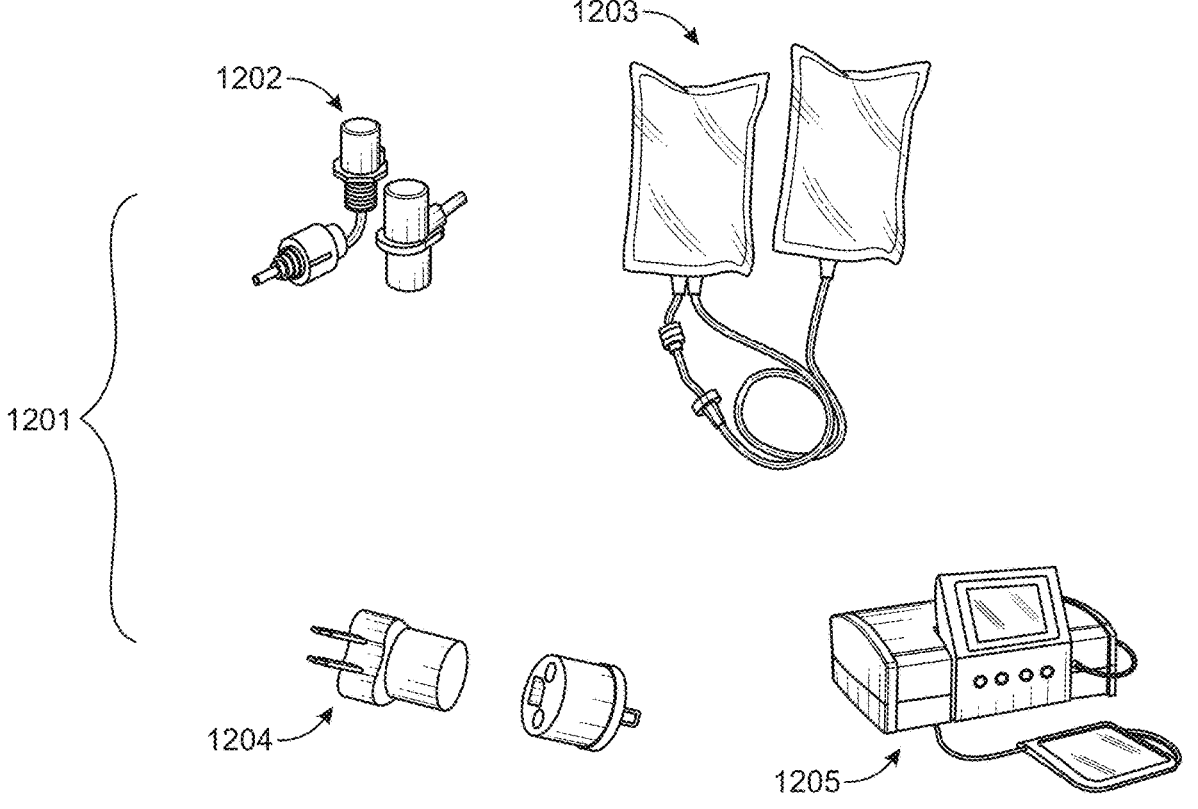
FIG. 12 shows optional dispensing options for using peritoneal dialysate generated by the present invention.

As illustrated in FIG. 12, the described systems can be used with alternative dispensing options. The sterile peritoneal dialysate 1201 can be dispensed through connectors 1202 to a sterile dialysate bag 1203 or other sterile dialysate container. The connectors 1202 can be single use or disposable connectors that provide transfer of sterile fluids. A non-limiting example of connectors that can be used with the described system is the Lynx®-Millipore connectors available from Merck KGaA, Darmstadt, Germany. Alternatively, the system can include a direct connection through connectors 1204 to an external cycler 1205 for immediate use of the generated peritoneal dialysate. The direct connection to an external cycler can use any type of connectors 1204 known in the art. The connectors 1204 can be single-use or reusable connectors and should provide for sterile transfer of fluids. The connectors 1204 should preferably be closed connectors, to avoid contact between the fluids and the external environment. A non-limiting example of a connector that can be used for a direct connection to an external cycler is the INTACT® connectors provided by Medinstill Development LLC Delaware, US.

The connectors can include connectors for connection to reservoirs, containers, or a tap or faucet. FIG. 11 illustrates non-limiting embodiments of connectors for connection to one or more containers. The connectors can be any type of connector that can form a seal with a container, tap, or faucet that serve as the fluid sources in the system. The connectors can be screw-type connectors that screw onto the containers, faucet or tap, snap-type connectors that snap onto the containers, faucet, or tap, or any other type of connector known in the art. O-rings or other sealing members can be included in the connectors to form a water-tight seal with the containers, faucet, or tap.

For connection to a tap or faucet, the connectors should be able to form a seal with standard at-home faucets. Further to this end, the connectors can include an adjustable bore, wherein the size of the opening of the connector for connection to the tap or faucet can be increased or decreased to adjust to different size faucets. Nuts, screws, or other tight-enable components can be included on the sides of the connectors allowing a user to tighten the connector around the faucet or tap regardless of the circumference of the faucet or tap. An o-ring or other sealing member can be placed on the faucet or tap to increase the effectiveness of the seal formed with the connectors.

Alternatively, a fitting can be screwed onto, or otherwise affixed to the faucet with a male end of the fitting extending outwardly from the faucet. The male end of the fitting can be inserted into the water line, and secured with an adjustable bolt, wire, or other tightening mechanism to ensure a proper seal.

For connection to a drain as illustrated in FIG. 10, the tubing for carrying waste fluids can simply be placed into the drain, bathtub, or other receptacle containing a drain for disposal. Alternatively, the tubing can include a connector for forming a sealable connection to a drain, ensuring that all waste fluids are directed into the drain.

One skilled in the art will understand that various combinations and/or modifications and variations can be made in the described systems and methods depending upon the specific needs for operation. Moreover, features illustrated or described as being part of an aspect of the invention may be used in the aspect of the invention, either alone or in combination, or follow a preferred arrangement of one or more of the described elements.

We claim:
1. A system, comprising:
a peritoneal dialysate generation cabinet, the peritoneal dialysate generation cabinet configured to house:
a peritoneal dialysate generation flow path, wherein the peritoneal dialysate generation flow path is configured to receive water from a water source, the water source fluidly connectable to an inlet of the peritoneal dialysate generation flow path, wherein the peritoneal dialysate generation flow path comprises:

one or more water purification modules fluidly connectable to the peritoneal dialysate generation flow path downstream of the water source, the one or more water purification modules configured to purify the water from the water source and output a purified water downstream to a first conduit;
at least two concentrate sources fluidly connectable to the first conduit of the peritoneal dialysate generation flow path through a first concentrate line, wherein the at least two concentrate sources each contain one or more solutes, wherein the at least two concentrate sources comprise at least one osmotic agent;
at least one valve positioned in the first concentrate line, wherein the at least one valve is configured to fluidly connect the first concentrate line to the first conduit to add a concentrate from each of the at least two concentrate sources to the purified water in the first conduit;
one or more pumps positioned in the first concentrate line, the one or more pumps configured to add the concentrate from the at least two concentrate sources to the purified water in the first conduit to generate peritoneal dialysate;
a sterilization module fluidly connectable to the first conduit downstream of the at least two concentrate sources and the one or more water purification modules;
wherein the first conduit fluidly connects the one or more water purification modules to the sterilization module;
wherein the first concentrate line is fluidly connected to the first conduit between the one or more water purification modules and the sterilization module; and
a control system, the control system programmed to add the at least one osmotic agent to the purified water in the first conduit, and the control system configured to determine a concentration of the at least one osmotic agent in the peritoneal dialysate in the first conduit, and the control system configured to adjust the one or more pumps to maintain a predetermined concentration of the at least one osmotic agent in the peritoneal dialysate in the first conduit based upon the determined concentration; and
at least one storage container;
wherein the at least one storage container is configured to be:
fluidly connectable to and fluidly disconnectable from an outlet of the peritoneal dialysate generation cabinet;
fluidly connectable to and fluidly disconnectable from a non-integrated cycler for conducting a peritoneal dialysis therapy,
wherein the non-integrated cycler is an external cycler which is not located within the peritoneal dialysate generation cabinet;
wherein, when the at least one storage container is connected to the peritoneal dialysate generation flow path of the peritoneal dialysate generation cabinet, the at least one storage container is located outside the peritoneal dialysate generation cabinet;
at least one valve configured to connect to the at least one storage container configured to selectively direct fluid to a desired container of the at least one storage container, wherein the system is configured to control the at least one valve to direct the fluid to the desired container based on the predetermined concentration of the at least one osmotic agent in the peritoneal dialysate and to direct the fluid to a second desired container based on a second predetermined concentration of the at least one osmotic agent in the peritoneal dialysate, wherein the predetermined concentration of the at least one osmotic agent is different than the second predetermined concentration of the at least one osmotic agent in the peritoneal dialysate.

2. The system of claim 1, further comprising one or more dialysate containers fluidly connectable to the peritoneal dialysate generation flow path downstream of the sterilization module.

3. The system of claim 1, wherein the at least two concentrate sources comprise at least two ion concentrate sources.

4. The system of claim 3, the at least two ion concentrate sources fluidly connectable to the first concentrate line; the system further comprising at least a second concentrate line having a second concentrate pump; the second concentrate line fluidly connectable to the at least one osmotic agent.

5. The system of claim 1, wherein the at least two concentrate sources comprises at least one ion concentrate source; the system further comprising at least a second concentrate line having a second concentrate pump; the second concentrate line fluidly connectable to the at least one ion concentrate source.

6. The system of claim 1, wherein the at least two concentrate sources comprises at least one ion concentrate source; and wherein the at least one ion concentrate source comprises one or more from the group consisting of sodium chloride, sodium lactate, magnesium chloride, calcium chloride, potassium chloride, and sodium bicarbonate.

7. The system of claim 1, wherein the at least one storage container comprises one or more sterilized dialysate bags.

8. The system of claim 1, wherein the at least one storage container comprises a reusable bag, wherein the reusable bag is configured to be sterilized prior to being reused.

9. The system of claim 1, wherein the at least one storage container comprises stainless steel.

10. The system of claim 1, wherein the at least one storage container is configured to be fluidly reconnected to the outlet of the peritoneal dialysate generation flow path of the peritoneal dialysate generation cabinet.

11. The system of claim 1, wherein the at least one storage container is configured to be fluidly reconnected to the non-integrated cycler for conducting the peritoneal dialysis therapy.

12. The system of claim 1, wherein the peritoneal dialysate generation cabinet is dimensioned to be positioned on a table.

13. The system of claim 1, wherein the peritoneal dialysate generation cabinet comprises a door configured to be open when in use and to be closed when not in use.

14. A system comprising:
a peritoneal dialysate generation cabinet, wherein the peritoneal dialysate generation cabinet is configured to house at least:
a water purification module;
a concentrate source; and
a sterilization module;
wherein the water purification module, the concentrate source, and the sterilization module are fluidly connectable to each other by a fluid flow path; and
at least one storage container,
wherein the at least one storage container is fluidly connectable to an outlet of the fluid flow path of the peritoneal dialysate generation cabinet;
wherein, when the at least one storage container receives a sterilized peritoneal dialysate from the peritoneal dialysate generation cabinet, the at least one storage container is configured to be:
fluidly disconnected from the outlet of the fluid flow path of the peritoneal dialysate generation cabinet; and
fluidly connected to a cycler for conducting a peritoneal dialysis therapy,
wherein the cycler is an external cycler which is not integrated with the fluid flow path of the peritoneal dialysate generation cabinet;
at least one valve configured to connect to the at least one storage container configured to selectively direct fluid to a desired container of the at least one storage container,
wherein the system is configured to control the at least one valve to direct the fluid to the desired container based on a predetermined concentration of at least one osmotic agent in the peritoneal dialysate and to direct the fluid to a second desired container based on a second predetermined concentration of the at least one osmotic agent in the peritoneal dialysate,
wherein the predetermined concentration of the at least one osmotic agent is different than the second predetermined concentration of the at least one osmotic agent in the peritoneal dialysate.

15. The system of claim 14, wherein the at least one storage container comprises one or more sterilized dialysate bags.

16. The system of claim 14, wherein the at least one storage container comprises a reusable bag, wherein the reusable bag is configured to be sterilized prior to being reused.

17. The system of claim 14, wherein the at least one storage container comprises a stainless steel.

18. The system of claim 14, wherein the at least one storage container is configured to be fluidly reconnected to the outlet of the fluid flow path of the peritoneal dialysate generation cabinet.

19. The system of claim 14, wherein the at least one storage container is configured to be fluidly reconnected to the cycler for conducting the peritoneal dialysis therapy.

20. The system of claim 14, wherein the peritoneal dialysate generation cabinet comprises a door configured to be open when in use and to be closed when not in use.

* * * * *